(12) United States Patent
Eda et al.

(10) Patent No.: US 6,828,158 B2
(45) Date of Patent: Dec. 7, 2004

(54) MICROPARTICLE ENHANCED LIGHT SCATTERING AGGLUTINATION ASSAY

(75) Inventors: Shinichi Eda, Kaiseraugst (CH); Jörg Heinrich Kaufmann, Rheinfelden (DE); Stefan Pohl, Grenzach-Wyhlen (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 143 days.

(21) Appl. No.: 09/827,846

(22) Filed: Apr. 6, 2001

(65) Prior Publication Data

US 2001/0026945 A1 Oct. 4, 2001

Related U.S. Application Data

(62) Division of application No. 09/129,744, filed on Aug. 5, 1998, now Pat. No. 6,248,597.

(30) Foreign Application Priority Data

Aug. 11, 1997  (EP) ............................................. 97113873

(51) Int. Cl.$^7$ ........................................... G01N 33/543
(52) U.S. Cl. ........................... 436/518; 435/6; 435/7.1; 435/7.5; 435/7.92; 435/7.94; 435/962; 436/518; 436/501; 436/523; 436/524; 436/528; 436/533; 436/539; 436/172; 422/52; 422/73; 422/82.05; 422/82.08; 422/82.09
(58) Field of Search ............................... 436/501, 518, 436/523, 524, 528, 533, 539, 172, 6, 7.1, 7.5, 7.92, 7.93, 7.94, 962; 422/52, 73, 82.05, 82.08, 82.09, 83

(56) References Cited

U.S. PATENT DOCUMENTS

| 4,210,723 A | | 7/1980 | Dorman et al. |
| 4,556,642 A | * | 12/1985 | Collet-Cassart et al. .... 136/500 |
| 4,590,169 A | | 5/1986 | Cragle et al. |
| 4,595,661 A | | 6/1986 | Cragle et al. |
| 5,330,891 A | * | 7/1994 | Sutton et al. .................. 435/5 |

FOREIGN PATENT DOCUMENTS

| WO | WO 89/11101 | 11/1989 |

OTHER PUBLICATIONS

Kapmeyer, Wolfgang et al. An automated particle–enhanced nephelometric assay for the quantitative determination of PSA, Clinical Chemistry, (1996) vol. 42, No. 6, PART 2, pp. S268–S269.*
Harchali et al. Micropaticle enhanced nephelometric immunoassay of anti–thyroid peroxidase autoantibodies in Thyroid disease CLin. Chem. 40(3): 422–447 (1994).*
Singer et al., American Journal of Medicine, vol. 21, pp. 888–892 (1956).
Deželićet al., Eur. J. Biochem., vol. 20, pp. 553–560 ( 1971).
Grange et al., Journal of Immunological Methods, vol. 18, pp. 365–375 (1977).
Eda et al., Progress in Clinical Biochemistry, pp. 265–267 (1992).
Winkles et al., Clinical Chemistry, vol. 35, No. 2, pp. 303–307 (1989).
Armbruster et al., Journal of Analytical Toxicology, vol. 16, pp. 172–175 (1992).
Lindmo et al., Journal of Immunological Methods, vol. 126, pp. 183–189 (1990).
Newman et al., Ann. Clin. Biochem., vol. 29, pp. 22–42 (1992).
Armbruster et al., Clinical Chemistry, vol. 40, No. 7, pp. 1233–1238 (1994).
Devey et al., Encyclopedia of Immunology, pp. 33–35 (1992).
Steward et al., Handbook of Experimental Immunology, vol. 1, ch. 25, pp. 1–30.
Fägerstam et al., Journal of Chromatography, vol. 597, pp. 397–410 (1992).
Chase, Methods of Immulogy and Immunochemistry, ch. 2, 197–209 (1967).
Köhler et al., Nature, vol. 256, pp. 495–497 (1975).
Galfré et al., Methods in Enzymology, vol. 73, pp. 3–46 (1981).
Boulianne et al., Nature, vol. 312, pp. 643–646 (1984).
Winter et al., Nature, vol. 349, pp. 293–299 (1991).
Huston et al., Proc. Natl. Acad. Sci. USA, vol. 85, pp. 5879–5883 (1988).
Nisonoff et al., Archives of Biochemistry and Biophysics, vol. 89, pp. 230–244 (1960).
Porter, Biochemical Journal., vol. 73, pp. 119–126 (1959).
Harlow et al., Antibodies: A Laboratory Manual, ch. 15, pp. 626–631 (1988).
Yamamoto et al., Veterinary Immunology and Immunopathology, vol. 36, pp. 257–264 (1993).
Sensabaugh et al., The Journal of Urology, vol. 144, pp. 1523–1526 (1990).
Daiss et al., Methods: A Companion to Methods in Enzymology, vol. 6, pp. 143–156 (1994).
Vigushin et al., J. Clin. Invest., vol. 91, pp. 1351–1357 (1993).

* cited by examiner

Primary Examiner—Chris Chin
Assistant Examiner—Gailene R. Gabel
(74) Attorney, Agent, or Firm—Gibbons, Del Deo, Dolan, Griffinger and Vecchione

(57) ABSTRACT

Reagents and the use of the reagents in a microparticle light scattering agglutination assay are disclosed. The reagents comprise a mixture of particles having relatively stronger light scattering properties and particles having relatively weak light scattering properties with respect to one another. The particles having strong light scattering properties carry a binding partner of high reactivity with the analyte. The particles having weak light scattering properties carry a binding partner of low reactivity with the analyte.

10 Claims, 8 Drawing Sheets

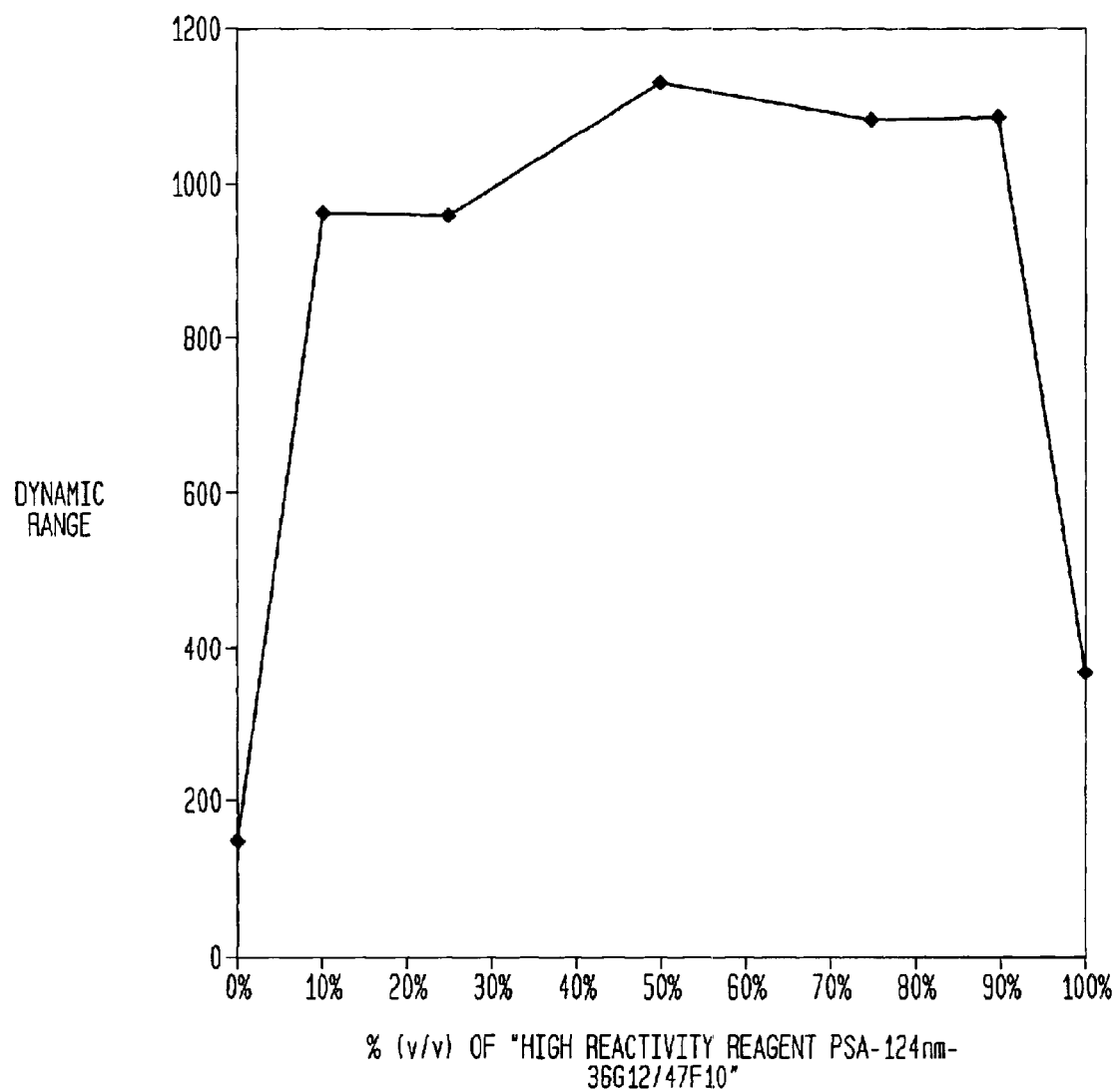

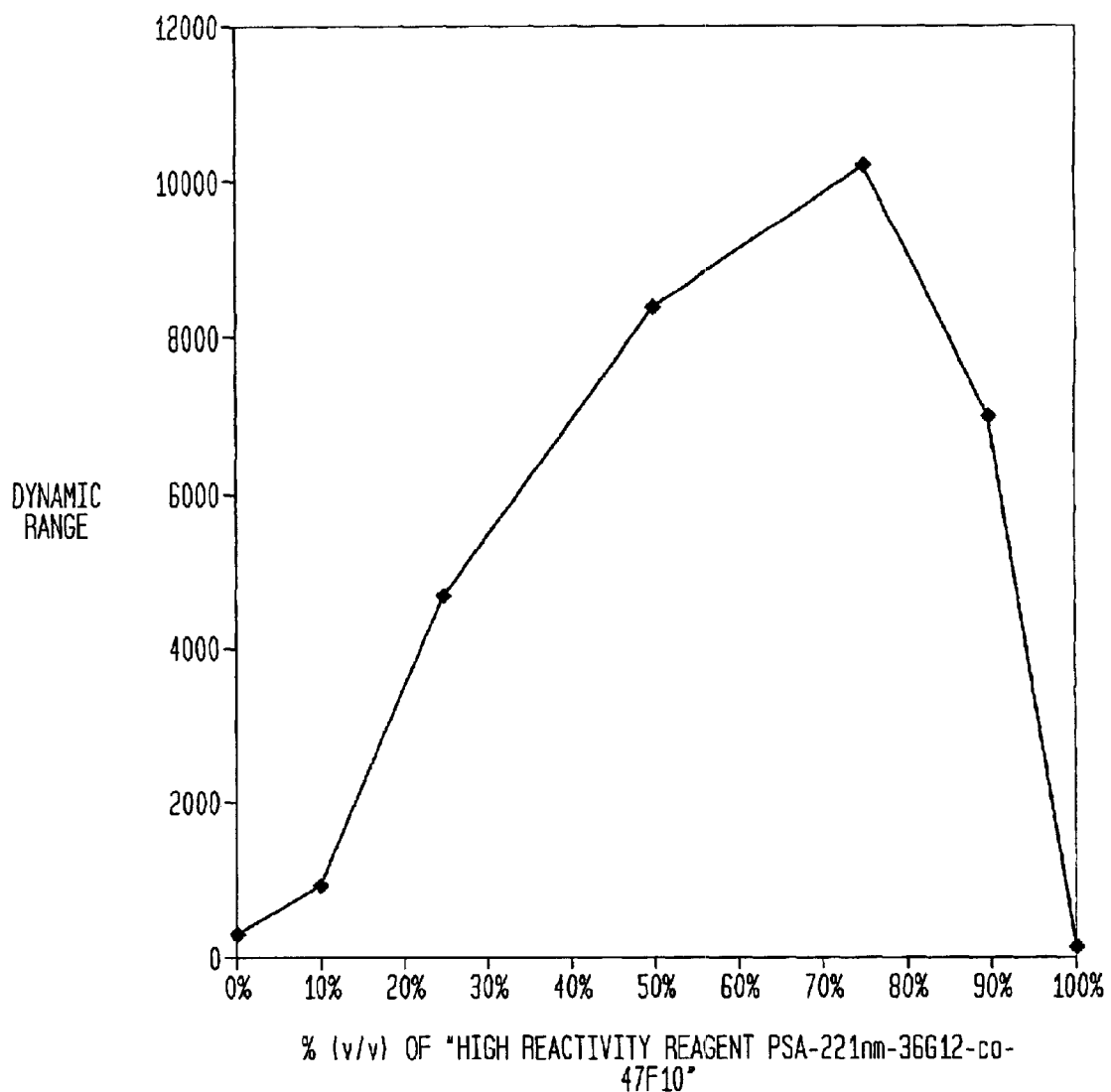

MICROPARTICLE ENHANCED LIGHT SCATTERING AGGLUTINATION ASSAY

REFERENCE TO RELATED APPLICATION

This application is a divisional of U.S. Ser. No. 09/129,744, filed Aug. 5, 1998, now U.S. Pat. No. 6,248,597, issued Jun. 19, 2001.

BACKGROUND AND SUMMARY OF THE INVENTION

The invention relates to a new microparticle enhanced light scattering agglutination assay for determining the amount of an analyte, and a microparticle reagent for performing that assay.

Microparticle agglutination tests were first described for the detection of rheumatoid factors by Singer J. and Plotz C., 1956, Am. J. Med. 21, 888–892, following the advent of reliable production methods for producing uniform latex particles of a wide range of sizes. Detection of the agglutination reaction by turbidimetry or nephelometry then made possible the development of truly quantitative microparticle enhanced light scattering agglutination tests, as described by Dezelic G. et al, 1971, Eur. J. Biochem. 20, 553–560, and Grange J. et al, 1977, J. Immunol. Methods, 18, 365–75.

The microparticle enhanced light scattering agglutination tests are quasi-homogeneous and do not need a separation and washing step at all. They thus meet the requirements for automation with commonly used clinical chemistry analyzers or dedicated nephelometers. Such tests provide an increased sensitivity by a factor of 2 to 3 orders of magnitude (down to $10^{-11}$ mol/l analyte) compared to direct agglutination tests not using microparticles and, in addition, less matrix interference and higher flexibility.

Due to the favorable characteristics described above, microparticle enhanced light scattering agglutination tests are now routinely used for quantifying proteins such as tumor markers (see, for example, Eda S. et al., 1993, Japanese J. Clin. Chem. 22, 99–103, or, 1992, in "Progress in Clinical Biochemistry" K. Miyai et al., pp. 265–267, Elsevier Publishers, Amsterdam, The Netherlands), specific proteins (see, for example, Winkes J. W. et al., 1989, Clin. Chem. 35/2, 303–307 or Chirot L. et al, 1992, Ann. Biol. Chim. 50, 143–147), drugs of abuse (see, for example, Ambruster D. et al., 1992, J. Anal. Toxicol. 16, 172–175) and therapeutic drugs (see, for example, "RDS Method Manual COBAS® INTEGRA® 1996: Digoxin", F. Hoffmann-La Roche A. G., Basle, Switzerland).

However, a drawback of microparticle enhanced light scattering agglutination assays is their limited dynamic range. Dynamic range, defined as the ratio of the upper measuring limit to the detection limit, is usually for those assays of only two orders of magnitude. Due to this limited dynamic range, the initial measurement often fails, requiring re-testing under different dilution degrees of samples. The limited dynamic range thus causes additional expense and loss of time, both of which are critical in laboratories performing those assays.

The problem addressed by the invention is therefore to provide a microparticle enhanced light scattering agglutination assay, and a microparticle reagent for performing that assay, that offer a larger dynamic range than heretofore known microparticle enhanced light scattering agglutination tests.

U.S. Pat. No. 4,595,661 describes a heterogeneous sandwich immunoassay wherein the hook effect, that is, a decrease of the signal at high antigen concentrations, is avoided by using an insoluble catcher antibody, and two soluble tracer antibodies having different affinities and different specificities to the antigen, the antibody of a lesser affinity making a significant contribution only at high antigen concentrations and thus forestalling the hook effect. That document states that the two exemplified assays according to the invention have the same dynamic range as those of the prior art (see column 6, lines 42–43 and column 8, lines 14–15).

PCT Patent Publication No. 89/11101 relates to an assay by flow cytometry which uses two distinguishable particles, for example particles of different sizes, as solid phase carriers of immunological binding partners having the same specificity but a different affinity for the same analyte. Different sizes of carrier particles are discriminated after separation in the capillary of the flow cytometry analyzer due to their different light scattering characteristics, which allows generation of two standard curves. That document and a subsequent publication of the inventor, T. Lindmo, 1990, J. Immunol. Methods 126, 183–189, specifically describe an assay for carcinoembryonic antigen (CEA) which uses particles of 7 μm or 10 μm diameter, respectively coated with a high affinity antibody or a low affinity antibody which bind to the same epitope, and a soluble labeled third antibody as a conjugate directed against another epitope. The flow cytometer records the fluorescence intensity of the conjugate bound on both particle types, and plots two separate standard curves. The system allows for a high dynamic range using sophisticated instrumentation and meticulously designed powerful analytical software which enable analyzing the data as if two immunoassays were run independently in parallel, one with particles of 7 μm diameter coated with a high affinity antibody, which preferably binds the antigen at first and whose standard curve works at low concentrations of analyte, and another with particles of 10 μm diameter coated with a low affinity antibody, whose standard curve works after the first standard curve flattens off.

Assays by flow cytometry and microparticle enhanced light scattering agglutination assays are based on totally different principles. In assays by flow cytometry there is no aggregation of microparticles and the amount of soluble labeled antibody is determined for each particle individually as they are separated and possibly, if they have distinguishing features, for example due to different sizes, discriminated by the flow cytometer; as many calibration curves are generated as there are particles with distinguishing features. In the microparticle enhanced light scattering agglutination assays there is a measuring as a whole, for example by turbidimetry or nephelometry, of the aggregation of binding partners bound to microparticles and analyte, without any possibility of determining the individual contribution of each particle or discriminating between particles having distinguishing features, and as a result only one calibration curve is generated.

The present invention will be further illustrated by the following examples. The following description will be better understood by referring to the following FIGS. 1A, 1B, 1C, 1D, 2, 3A, 3B and 4.

BRIEF DESCRIPTION OF THE FIGURES

FIG. 1A represents the variation of the dynamic range (DR) of a mixture of the following microparticle reagents: a 1/1 mixture of particles of 124 nm diameter coated with low reactivity monoclonal antibody 63C5 or 16B1 ("Low Reactivity Reagent PSA-124 nm-63C5/16B1"), and a 1/1 mixture of particles of 124 nm diameter coated with high reactivity antibody 36G12 or 47F10, ("High Reactivity Reagent PSA-124 nm-36G12/47F10"), as a function of the % (v/v) of the latter microparticle reagent.

FIG. 1D represents the variation of the DR of a mixture of a microparticle reagent of particles of 89 nm diameter co-coated with low reactivity monoclonal antibodies 63C5 and 16B1 ("Low Reactivity Reagent PSA-89 nm-63C5-co-16B1"), and a microparticle reagent of particles of 221 nm diameter co-coated with high reactivity antibodies 36G2 and 47F10 ("High Reactivity Reagent PSA-221 nm-36G2-co-47F10"), as a function of the % (v/v) of the latter microparticle reagent.

DETAILED DESCRIPTION OF THE INVENTION

Figure 1B:
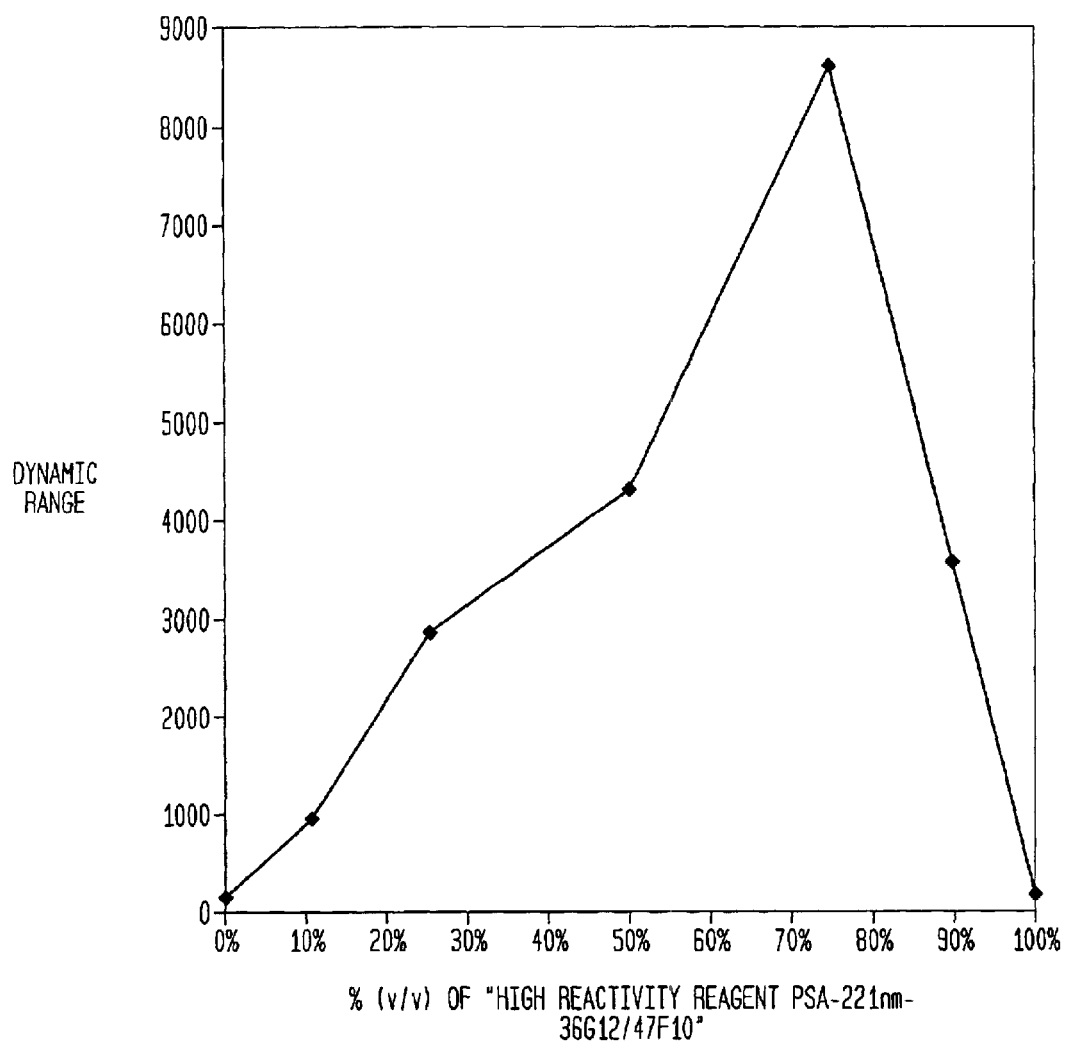
FIG. 1B represents the variation of the DR of a mixture of the following microparticle reagents: a 1/1 mixture of particles of 124 nm diameter coated with low reactivity monoclonal antibody 63C5 or 16B1 ("Low Reactivity Reagent PSA-124 nm-63C5/16B1"), and a 1/1 mixture of particles of 221 nm diameter coated with high reactivity antibody 36G12 or 47F10 ("High Reactivity Reagent PSA-221 nm-36G12/47F10"), as a function of the % (v/v) of the latter microparticle reagent.

The present invention provides a microparticle enhanced light scattering agglutination assay for determining the amount of an analyte, which comprises using a mixture of particles of strong light scattering properties carrying at least one binding partner of high reactivity for the analyte, and particles of weak light scattering properties carrying at least one binding partner of low reactivity for the analyte. The assay of the invention shows an unexpectedly high dynamic range (DR).

The expressions "particles of strong light scattering properties" and "particles of weak light scattering properties" mean microparticles of any size and any material, the scattering of light per particle being substantially more for the former particles than for the latter particles. The microparticles are usually approximately spherical with a narrow size distribution, a good representation of their size being their mean diameter. According to the laws of light scattering (D. J. Newman et al., 1992, Ann. Clin. Biochem. 29, 22–42), strong light scattering properties may result from a large particle size, or a high ratio of the refractive index of the particle to that of the medium, whereas weak light scattering properties may result from a small particle size, or a low ratio of the refractive index of the particle to that of the medium. Rayleigh law of light scattering for example (see D. J. Newman et al., above cited reference) is expressed by the following equation:

$$I = I_0 16\pi^4 R^4 ((n^2-1)/(n^2+2))^2 / r^2 \lambda^4,$$

wherein

I is the light intensity measured by the detector, $I_0$ is the light intensity propagating in the medium, $\lambda$ is the wavelength in the medium, R is the microparticle radius, r is the distance between the detector and scatterer, n is $n_1/n_0$, $n_1$ being the refractive index of particles and $n_0$ being the refractive index of the medium.

The size and/or the refractive index ratio of the microparticles is such that they can cause light scattering at the wavelength used for detection of agglutinated microparticles. That size is generally chosen to be substantially smaller or slightly smaller than that wavelength. The detection wavelength is usually from 300 nm to 1200 nm. The mean diameter of microparticles is suitably from 30 to 600 nm, preferably from 50 to 500 nm.

The particles of strong light scattering properties have preferably a larger size and/or a higher refractive index than the particles of weak light scattering properties.

According to one preferred embodiment of the invention, the "particles of strong light scattering properties" and the "particles of weak light scattering properties" are microparticles of the same size but made of different materials, the material of the former particles having a substantially higher refractive index than the material of the latter particles. The ratio of the refractive index of the particles of strong light scattering properties to that of the particles of weak light scattering properties is then suitably at least 1.2, preferably at least 1.5.

According to another preferred embodiment the "particles of strong light scattering properties" and the "particles of weak light scattering properties" are microparticles of the same material but having different sizes, the size of the former particles, hereafter referred to as "large particles", being substantially bigger than that of the latter particles, hereafter referred to as "small particles".

The mean diameter of the large particles is suitably from 160 to 600 nm, preferably from 190 to 500 nm. The ratio between the mean diameter of the large particles and the mean diameter of the small particles is suitably from 1.5 to 4.0, preferably from 1.7 to 3.2.

The total concentration of microparticles in the mixture will be selected according to methods well known in the art of microparticle enhanced light scattering immunoassays, so that absorbance values deriving from microparticles do not influence accurate and precise measurements but the microparticle concentration is high enough to get signal development. The ratio (w/w) between the concentration of large particles and the concentration of small particles in the mixture is suitably 0.01 to 5, preferably 0.05 to 2.

The material of the microparticles may be any inorganic, organic, or polymer material suitable for microparticle enhanced light scattering assays. Such materials include for example selenium, carbon, gold; nitrides of carbon, silicium or germanium, for example $Si_3N_4$; oxides of iron, titanium or silicium, for example $TiO_2$ or $SiO_2$; and polymeric materials such as, for example, polystyrene, polyvinyl chloride, epoxy resins, polyvinylidene chloride, polyalphanaphtyl methacrylate, polyvinylnaphtalene, or copolymers thereof, in particular copolymers of styrene and a copolymerizable ethylenically unsaturated compound, for example styrene-methacrylate co-polymers. Microparticles made of polymeric materials, as well as core-shell particles consisting of an inner core polymerized from styrene and an outer shell formed by copolymerization from styrene with a copolymerizable ethylenically unsaturated compound, as described for example in U.S. Pat. No. 4,210,723, are particularly suitable.

The assay of the invention can be any type of microparticle enhanced light scattering agglutination test, in particular a turbidimetric or nephelometric test.

The assay of the invention can be used for determining the amount of any analyte apt to be determined by a microparticle enhanced light scattering assay, that is, any analyte for which there are binding partners apt to be bound to microparticles which specifically recognize the analyte. Analytes that can be determined by the assay of the invention include antigenic analytes, the binding partners then suitably being immunological binding partners, and nucleic acids, the binding partners then suitably being oligonucleotide capture probes showing sufficient sequence complementarity for hybridization to take place.

The antigenic analyte may be monomeric or polymeric, with or without repetitive epitopes. Suitable antigenic analytes include:

(a) specific proteins such as for example, alpha-1-acid glycoprotein (AAGP), alpha-1-antitrypsin (AAT), albumin in serum (ALBS), microalbumin (ALBU), apolipoprotein A-1 (APOA), apolipoprotein B (APOB), antistreptolysin (ASO), antitrombin III, (AT III), complement C3C (C3C), complement C4 (C4), C-reactive Protein (CRP), fibrinogen (FIBG), fibronectin (FIBR), haptoglobulin (HAPT), immunglobulin A, G, M (IgA, IgG, IgM), lipoprotein A (LPA), rheumatoid factors (RF), transferrin (TRSF), serum amyloid A (SAA);

(b) tumor markers such as, for example, alpha-fetoprotein (AFP), human chorionic gonadotropin beta-subunit (b-HCG), beta-2-microglobulin, carbohydrate antigens such as CA 125, CA 15-3, CA 19-9, CA 72-4, carcinoembryonic antigen (CEA), ferritin, mucin-like carcinoma associated antigen (MCA), neuron specific enolase (NSE), prostate specific antigen (PSA);

(c) cardiovascular or fibrinolysis markers such as, for example, fatty acid binding protein (FABP), fibrin and fibrinogen degradation products (FDP), FDP D-dimer, troponin, myoglobin, glycated hemoglobin A1c (HbA1c);

(d) virus markers such as, for example, influenza virus, Herpes simplex virus (HSV);

(e) immunoglobulin E (IgE), insulin, cystatin C.

Suitable nucleic acid analytes include DNA, RNA and derivatives thereof, the determination of the amount of which is of interest in the diagnostic or pharmaceutical field. Examples of such nucleic acids that can be quantitatively determined using the assay of the invention are HIV1-RNA, HIV2-RNA, HCV-RNA, enterovirus RNA, HTLV-DNA, CMV-DNA and Mycobacterium tuberculosis DNA.

Nucleic acid analytes are in many cases present only in minute quantities in body fluids. A nucleic acid amplification reaction, for example using polymerase chain reaction (PCR), ligase chain reaction (LCR), transcription amplification or self-sustained sequence replication, is therefore generally performed prior to determining the amount of the analyte by the assay of the invention. Preferably this amplification is performed by PCR (see "PCR Protocols: A Guide to Methods and Applications" M. A. Innis et al., 1990, Academic Press, NY, USA.) which comprises the following steps: (1) oligonucleotide primers which determine the ends of the sequences to be amplified are annealed to single-stranded nucleic acids in a test sample, (2) a nucleic acid polymerase extends the 3'-ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension and product denaturation are repeated enough times to generate easily identified and measured amounts of the sequences defined by the primers.

The double stranded amplified nucleic acid after denaturation can be quantified by the assay of the invention.

The expressions "binding partner of high reactivity for the analyte" and "binding partner of low reactivity for the analyte", mean binding partners apt to react with the analyte so as to form a binding complex, the reactivity under the conditions of the assay being higher for the former than for the latter binding partner.

A convenient parameter that reflects the reactivity of a binding partner under the conditions of a microparticle enhanced light scattering assay is the detection limit (DL) of that assay using particles coated with that binding partner. The DL is defined as the minimum analyte concentration which is discriminable from standard 0 or negative control with a defined probability. That parameter is calculated statistically based on a number of replicates of the dose-response curves, for example using the 2 or 3 SD method described by D. A. Armsbruster et al., 1994, Clin. Chem. 40, 1233–1238.

The ratio of the detection limits of the assays performed with microparticles of the same size and the same material, coated independently with the binding partner of high reactivity and the binding partner of low reactivity, is suitably 0.01 to 0.5, preferably 0.03 to 0.4.

Other methods of determining the reactivity of binding partners may also be used depending upon the nature of the analyte and that of the binding partners.

For a nucleic acid analyte and oligonucleotide capture probes as binding partners, the reactivity of the latter can generally reliably be controlled by the choice of the lengths of the probes and their degrees of complementarity with the target nucleic acid taking into account known possible variants thereof. Oligonucleotide capture probes of high reactivity and oligonucleotide capture probes of low reactivity are directly or via a spacer covalently bound to particles of strong light scattering properties and particles of weak light scattering properties, respectively.

For an antigenic analyte and an immunological binding partner, the functional affinity of the latter is also a convenient parameter that generally gives a good approximation of its reactivity under the conditions of a microparticle enhanced light scattering assay. The functional affinity of the binding partners to the antigenic analyte can be measured by determining their apparent dissociation constants by commonly used methods well known in the art, for example using a BIAcore™ instrument (Pharmacia, Sweden), equilibrium dialyses, relative affinity titrations in ELISA systems, as described notably in I. M. Roitt and M. E.

Devey, "Encyclopedia of Immunology", 1992, 33–35, eds. I. M. Roitt and P. J. Delves, Academic Press, London, UK, or M. W. Steward et al, 1986, "Handbook of Experimental Immunology" Vol. 1, chapter 25, pp. 1–30, ed. D. M. Weir, Oxford: Blackwell Scientific Publications, Oxford, UK. The term "apparent" here refers to a simplified $A+B=AB$ equilibrium model, without consideration of the possible repetitive epitopes of the analyte (L. G. Fägerstam et al., 1992, Journal of Chromatography, 597, 397–410).

The ratio of the apparent dissociation constants of the immunological binding partner of high reactivity and the immunological binding partner of low reactivity, is suitably from 0.01 to 0.5, and preferably from 0.05 to 0.2.

Immunological binding partners that can be used in the assay of the invention include polyclonal antibodies of any species, monoclonal antibodies of any species (including chimeric antibodies and/or recombinant antibodies) or fragments thereof, for example Fab, Fab' or $F(ab')_2$ fragments. Because of their capacity of being produced identically in unlimited amounts, monoclonal antibodies or fragments thereof are generally preferred.

For antigenic analytes without repetitive epitopes, when using monoclonal antibodies or fragments thereof as immunological binding partners, it is generally necessary to use at least two binding partners of high reactivity and two binding partners of low reactivity, the two binding partners of high reactivity being directed to different epitopes from one another and the two binding partners of low reactivity being directed against different epitopes from one another, so that a sandwich complex immunoagglutinate between both binding partners of high reactivity and between both binding partners of low reactivity can be formed. The particles with strong light scattering properties can either be co-coated with the two binding partners of high reactivity or separately coated for part of the particles with one, for the remaining part of the particles with the other, of those binding partners. The particles with weak light scattering properties can either be co-coated with the two binding partners of low reactivity or separately coated for part of the particles with one, for the remaining part of the particles with the other, of those binding partners.

For antigenic analytes with repetitive epitopes, when using monoclonal antibodies or fragments thereof as immunological binding partners, it is generally sufficient to use one binding partner of high reactivity coated on particles with strong scattering properties and one binding partner of low reactivity coated on particles with weak scattering properties. The binding partner of high reactivity and the binding partner of low reactivity can be directed against the same or different epitopes, since a sandwich complex immunoagglutinate is prone to be formed in any case because of the repetitive epitope of the analyte.

Preparation of Immunological Binding Partners

Polyclonal antibodies can be prepared by methods well known in the art, such as those described for example by Chase, M. W., 1967, in "Methods of Immunology and Immunochemistry", ed. Williams, A. et al., M. W., pp. 197–209, Academic Press, New York. Briefly, animals of a species (for example rabbits, goats, or sheep) are repetitively immunized with purified antigen in an appropriate adjuvant, for example Freund's adjuvant. After immunization the animals are bled and the polyclonal antibodies are purified by methods such as, for example, ammoniumsulfate-precipitation, anionic exchange chromatography, immunaffinity chromatography, and/or affinity chromatography.

Monoclonal antibodies can be prepared by methods well known in the art, notably those described by G. Köhler et al., 1975, Nature 256, 495, G. Galfre et al., 1981, Meth. Enzymol. 73, 3–46, or R. Kennet, 1980, in: "Hybridomas: a new dimension in biological analysis", ed. R. Kennet et al., Plenum press, New York & London. Briefly, spleen cells or peripheral blood cells from immunized mice or rats are fused with a myeloma cell line, using for instance the polyethylene fusion method. After fusion, the cells are grown on culture plates and a selection of correctly fused cells is performed using, for example, hypoxanthine/aminopterin/thymidine (HAT) selection. Antibody producing cell lines are identified by methods such as EIAs, RIAs or agglutination assays. After identification of the antibody producing cell line, the cells are repeatedly subcloned by the method of limited dilution to guarantee that the new growing cell line derives from one single cell.

Chimeric antibodies can be obtained by methods well known in the art such as that described by G. L. Boulianne et al., 1984, Nature 312, 643–645. The procedure can be briefly described as follows. The DNA of the antigen-binding site from a monoclonal antibody of one species or parts thereof are transferred to the DNA of the antibody framework of another antibody of a different species. This new construct is cloned into an expression vector, which is transferred to the corresponding expression system to produce the antibody.

Recombinant antibodies can be obtained without using animal vehicles by methods known in the art, such as those described by G. Winter et al., 1991, Nature, 349, 293 or J. S. Huston et al., 1988, Proc. Ntl. Acad. Sci. USA, 85, 5879. Those methods involve the following steps: introduction of DNA (cDNA or synthetic DNA) coding for an antibody or fragments thereof into a host cell, for example *E. coli*, fungi, yeast, plants or eucaryotic cells, selection of antibodies with the desired specificity and affinity and expressing the antibody or fragment thereof in the corresponding expression system.

Fab-, Fab'-, and $F(ab')_2$-fragments of polyclonal antibodies of any species, monoclonal antibodies of any species (including chimeric antibodies and/or recombinant antibodies) can be prepared by methods well known in the art, such as those described, for example, by A. Nissonoff et al, 1960, Arch Biochem Biophys, 89, 230, or R. P. Porter, 1959, Biochem J, 73, 119, or E. Harlow et al, 1988, in "Antibodies—A Laboratory Manual", 626–631, Cold Spring Harbour Press, New York, USA.

Selection of Immunological Binding Partners of Different Reactivities to the Analyte When using monoclonal antibodies or fragments thereof as binding partners, the selection of the immunological binding partners of high reactivity and low reactivity can conveniently be performed by coating each of the immunological binding partners separately onto microparticles of the same material and size, followed by mixing the microparticle reagents in a given ratio, for example 1/1 v/v, in a pernutative manner in case two immunological binding partners of high reactivity and two immunological binding partners of low reactivity are needed to cause agglutination. After generating calibration curves of the microparticle reagent under the same conditions, the steepness of the resulting calibration curves for low concentrations of analyte give a first indication of the reactivity of the immunological binding partners.

When using polyclonal antibodies as binding partners, the preparation of high and low reactivity polyclonal antibodies may be performed according to methods well known in the art by introducing the polyclonal antibodies into an affinity chromatography column carrying the antigenic analyte covalently bound to the gel matrix. With a gradient of elution buffer, low reactivity polyclonal antibody fractions will elute first from the column, followed by fractions with increasingly higher reactivity (see S. Yamamoto et al., 1993, "Veterinary Immunology and Immunopathology" 36, 257–264, Elsevier Science Publishers B. V., Amsterdam). Reactivity of the fractions can then be checked either with a BIAcore™ instrument or by coating them independently onto microparticles of the same size and material and generating the corresponding calibration curves.

Selection of antibodies can be done by the above mentioned procedure of coating them on microparticles followed by a detection limit analysis or a determination of its functional affinity as described above. The ratio of the detection limits of the assays performed with microparticles of the same size and the same material, coated independently with the binding partner of high reactivity and the binding partner of low reactivity, is suitably 0.01 to 0.5, preferably 0.03 to 0.4. The ratio of the apparent dissociation constants of the immunological binding partner of high reactivity and the immunological binding partner of low reactivity, is suitably from 0.01 to 0.5, and preferably from 0.05 to 0.2.

Coating of Microparticles with the Immunological Binding Partners

The coating of the immunological binding partners onto the microparticles can be performed adsorptively or covalently according to methods well known in the art which meet the properties of the material used.

The invention also relates to a microparticle reagent suitable for performing the above defined assay. That reagent comprises a mixture of microparticles of 30 to 600 nm in diameter, including particles of strong light scattering properties carrying at least one binding partner of high reactivity for the analyte and particles of weak light scattering properties carrying at least one binding partner of low reactivity for the analyte. That mixture is usually kept in suspension in a buffer comprising a detergent (for example, TWEEN® 20 or TRITON® 100) and an antibacterial agent such as, for example, sodium azide or potassium azide.

The invention also concerns a method of preparing the above microparticle reagent which comprises mixing microparticles of 30 to 600 nm in diameter having strong light scattering properties and carrying at least one binding partner of high reactivity partner for the analyte and microparticles of 30 to 600 nm in diameter having weak light scattering properties and carrying at least one binding partner of low reactivity for the analyte.

EXAMPLE 1

Increase of the dynamic range of a microparticle enhanced light scattering immunoagglutination assay for Prostate Specific Antigen (PSA).
1) Methods and Reagents
   a) Preparation of Monoclonal Antibodies to Different Epitopes of PSA Having Different Affinities Prostate Specific Antigen (PSA) is a serum component that is widely clinically used for monitoring prostate cancer. PSA is a 34 kDa glycoprotein consisting of a single polypeptide chain which appears in serum either free or complexed with antichymotrypsin.

Monoclonal antibodies to PSA were prepared by methods well known in the art, described, for example, by Harlow et al., 1988, Section 6 of "Antibodies: a Laboratory Manual", Cold Spring Harbor Press, New York, USA. Human PSA was isolated from human seminal plasma as described Sensabaugh et al., 1990, J. Urology 144, 1523. Mice were immunized in regular intervals with 4 injections of 50 µg human PSA in RAS (RIBI adjuvant system). Four months after the first injection, lymphocytes isolated from the spleen of the immunized mice were fused with the myeloma cell line SP2/0-Ag 14 using the polyethyleneglycol method as described by G. Galfré et al., 1981, Methods in Enzymology 73, 3–46.

Hybridomas secreting an antibody against PSA were identified by the following screening ELISA: microtiter-plates were coated with rabbit anti-human-PSA immunoglobulin; PSA bound to this solid phase was incubated with the supernatants of the hybridoma cultures. Monoclonal antibody bound to PSA was detected using anti-mouse-immunoglobulin-peroxidase-conjugate.

130 hybridomas could be isolated, secreting antibodies against at least 7 different epitopes of human PSA. About 25 different monoclonal antibodies were purified and were characterized in more detail.

Epitope binding was performed and the relative reactivity of the antibodies was determined in terms of their apparent dissociation constants, using the BIAcore™ biosensor technology (Pharmacia, Sweden). The latter is based on the surface plasmon resonance technique (see J. L. Daiss et al., 1994, in "Methods: A Companion to Methods in Enzymology" 6, 143–156, Academic Press Inc., New York, USA) and allows one to monitor the kinetics and stochiometry of biomolecular reactions. Starting from cell culture supernatants, the monoclonal antibodies were bound to the biosensor surface via polyclonal rabbit anti-mouse-Fc-antibody. Association and dissociation of the antigen PSA to the monoclonal antibodies were monitored. The data were analysed using the inherent BIA evaluation software, based on the simple A+B=AB equilibrium model (L. G. Fägerstam et al., 1992, Journal of Chromatography, 597, 397–410).

The pair of high affinity monoclonal antibodies 36G12 and 47F10 having respectively apparent dissociation constants of 0.6 nM and 0.5 nM and the pair of low affinity monoclonal antibodies 63C5 and 16B1 having dissociation constants of 3.7 and 5.6 nM were selected for coating the microparticles. Monoclonal antibodies 36G12 and 63C5 recognize epitopes that are different from the epitopes recognized by monoclonal antibodies 47F10 and 16B1, all those epitopes being present in both the free form and the complexed form of PSA. The hybridomas producing monoclonal antibodies 36G12, 47F10, 63C5 and 16B1 were deposited in accordance with the Budapest Treaty on Jun. 2, 1997 at the DSMZ under the numbers ACC2314, ACC2315, ACC2316 and ACC2313, respectively.

b) Preparation of Microparticle Reagents

The coating procedure used is a modification of the procedure described in the publication from Seradyn Inc., Indianopolis, USA: "Microparticle Reagent Optimization: a Laboratory Reference Manual from the Authority on Microparticles", 1994, 66–73.

Carboxymodified polystyrene spherical particles having respectively a diameter of 89, 124 or 221 nm (available from Seradyn Inc., Indianapolis, USA, under reference numbers C9553/20, 2280 and 532G) were diluted to a 2% w/v suspension with 20 mM 2-(N-morpholino) ethanesulfonic acid (MES), pH 6.1, and washed twice in that buffer by centrifugation.

For each particle size 750 µl of the washed solution were sonicated with a tip sonicator for 30 seconds (ice bath, 10 seconds interval) and activated with 1-ethyl-3-(3-dimethylaminopropyl)-car (EDC)/sulfo-N-hydroxysuccimide (s-NHS) by the addition of 30 µl of a solution of 30 mM EDC and 30 mM s-NHS. The reaction mixture was incubated for 1 hour at 20° C. on a roller. The microparticle suspension was washed twice by centrifugation with 20 mM MES, pH 6.1. After every centrifugation step the microparticle pellet was resuspended with tip sonication for 30 seconds on ice.

The monoclonal antibodies were diluted to 3 mg/ml in 20 mM MES, pH 6.1. For coating, 750 µl of this solution was mixed with the activated microparticle suspension obtained above, vortexed intensively and incubated for 2 hours at 20° C. on a roller.

The coating reaction was stopped by the addition of 30 µl 2 M glycine, pH 11, and was incubated for 15 minutes. The microparticle suspension was washed twice by centrifugation with 50 mM glycine, pH 8, containing 0.03% Triton X-100 and 0.1% $NaN_3$. After every centrifugation step the micoparticle pellet was resuspended with tip sonication for 30 seconds (10 seconds interval, 20 microns amplitude) on ice. After the last centrifugation step the microparticle pellet was resuspended in the above buffer by tip sonication and diluted to a working concentration depending on the size of microparticle, namely for a diameter of 89 nm, 0.5% w/v (that is, 0.5 g/100 ml), for a diameter of 124 nm, 0.2% w/v and for a diameter of 221 nm, 0.1% w/v. That working concentration was chosen so as to have an optical density (OD) blank value at cycle 5 between 0.35 and 0.45 (see c) below).

c) Determination of the Calibration Curve and Calculation of the Detection Limit (DL), Upper Measuring Limit (UML) and Dynamic Range (DR).

All measurements of immunoagglutination reactions were performed at a wavelength of 550 nm on a COBAS® MIRA S clinical chemistry analyzer (Hoffmann-La-Roche A. G., Basel, Switzerland), using the reaction buffer of the following composition: 20 mM Tris/HCl, pH 7.4, 20 mM $CaCl_2$, 300 mM NaCl, 0.05% Tween® 20, 0.2% bovine serum albumine (BSA), 0.5% polyethylene glycol (PEG) and 0.1% NaN3 and the following parameter setting: (a) 120 µl of reaction buffer and 70 µl of microparticle suspension together with 20 µl water are pipetted into a cuvette during cycle 1; (b) after 2.1 minutes pre-incubation, the agglutination reaction starts with the addition of 15 µl standard solution (or sample) and 35 µl water in cycle 6; and (c) endpoint reading occurs at cycle 18 after 5 minutes' reaction. The result is calculated as the difference between the measured signal at cycle 18 and the reagent blank at cycle 5.

The dose-response curves were generated with single determinations and the data processed and plotted with EXCEL™ 5.0 software.

Measurements of 11 replicates of the dose-response curves were performed for determination of the detection limit (DL) and the upper measuring limit (UML). A standard deviation of about 2 mOD was found.

The detection limit (DL) is here defined as the minimum analyte concentration which is discriminable from standard 0 with a probability of 95%. That parameter is calculated statistically using the two SD method described by D. A. Armsbruster et al., 1994, Clin. Chem. 40, 1233–1238.

The upper measuring limit (UML) of the dose-response curve is here defined as the last standard exceeding or equaling a signal difference of 20 mOD to the previous standard.

The dynamic range (DR) is the ratio between the UML and the DL.

In the experiments described in detail hereinbelow only one monoclonal antibody selected among 36G12, 47F10, 63C5 and 16B1 was used for coating particles of a given diameter.

2) Influence of Microparticle Size on the Calibration Curve

The calibration curves were plotted and the DL, UML and DR were determined for microparticle reagents of particles of diameter 89, 124 or 221 nm coated with the same amount of the same antibody to PSA, namely either one of high reactivity monoclonal antibodies 36G12 and 47F10 or one of low reactivity monoclonal antibodies 63C5 and 16B1.

The following tables 1a and 1b respectively set forth the optical density (OD) measured as a function of the PSA concentration (that is, the calibration curve data), and the DL, UML and DR for two such microparticle reagents, one of particles of diameter 89 nm coated with high reactivity monoclonal antibody 36G12 or 47F10 (mixture 50/50 v/v), the other of particles of diameter 221 nm coated with high reactivity monoclonal antibodies 36G12 and 47F10, and the 90/10 (v/v) mixture thereof.

As illustrated in Table 1b for particles of diameter 89 nm and particles of diameter 221 nm, the DL and the UML both decreased with particle size, as could be expected from the Rayleigh scattering theory. The particles of diameter 221 nm show a preferable low detection limit of 0.86 ng/ml PSA, but lacks in UML and DR due to the limited concentration of microparticles in the assay. Increasing the concentration is not feasible and would lead to an unacceptable high blank value.

Mixing the particles of diameter 89 nm and diameter 221 nm results in a slightly increased DR, with a maximum value of about 1275, obtained with a 90/10 (v/v) mixture ratio of 89 nm and 221 nm particles, hereafter referred to as "High Reactivity Reagent PSA-89 nm/221 nm-36G12/47F10", showing a relatively high detection limit of 14.62 ng/ml.

TABLE 1a

Calibration curve data for microparticle reagents of particles of 89 or 221 nm diameter, both coated separately with high reactivity mabs 36G12 or 47F10 and the 90/10% (v/v) mixture thereof.

| PSA concentration | | Optical density (OD 550 nm) | | |
|---|---|---|---|---|
| ng/ml | $10^{-14}$ mol/cuvette | Particles of 89 nm diameter | Particles of 221 nm diameter | Particles of 89 and 221 nm diameter (90/10 v/v mixture) |
| 0 | 0 | −0.001 | −0.01 | −0.006 |
| 10.75 | 0.5 | 0 | 0.046 | −0.002 |
| 21.5 | 1.0 | 0 | 0.105 | 0.001 |
| 43.0 | 2.0 | 0.004 | 0.179 | 0.005 |
| 86 | 4.0 | 0.01 | 0.262 | 0.009 |
| 172 | 8.0 | 0.019 | 0.314 | 0.02 |
| 344 | 16 | 0.04 | 0.317 | 0.044 |
| 1032 | 48 | 0.121 | 0.301 | 0.131 |
| 3096 | 144 | 0.36 | 0.283 | 0.38 |
| 9310 | 433 | 0.71 | 0.273 | 0.697 |
| 18640 | 867 | 0.828 | 0.28 | 0.798 |
| 27950 | 1300 | 0.867 | 0.279 | 0.813 |
| 41925 | 1950 | 0.853 | — | 0.79 |
| 55900 | 2600 | 0.748 | — | — |

TABLE 1b

Detection limit (DL), upper measuring limit (UML) and dynamic range (DR) for microparticle reagents of particles of 89 or 221 nm diameter, both coated with high reactivity mabs 36G12 or 47F10, and the 90/10% (v/v) mixture thereof.

| | DL (ng/ml) | UML (ng/ml) | DR |
|---|---|---|---|
| Particles of 89 nm | 43 | 27950 | 650 |
| Particles of diameter 221 nm | 0.86 | 175 | 200 |
| Particles of 89 and 221 nm diameter (90/10 v/v/ mixture) | 14.62 | 18640 | 1275 |

3) Influence of Antibody Reactivity on the Calibration Curve

Microparticle reagents, hereafter referred to as "High Reactivity Reagent 124 nm-PSA-36G12/47F10" and "Low Reactivity Reagent PSA-124 nm-63C5/16B1", were prepared by mixing equal volumes of microparticle reagent of particles of diameter 124 nm coated with high reactivity monoclonal antibody 36G12 and microparticle reagent of particles of diameter 124 nm coated with high reactivity monoclonal antibody 47F10, and by mixing equal volumes of microparticle reagent of particles of diameter 124 nm coated with low reactivity monoclonal antibody 63C5 and microparticle reagent of particles of diameter 124 nm coated with low reactivity monoclonal antibody 16B 1, respectively.

The calibration curves (see raw data on Table 2a) were plotted and the DL, UML and DR were determined for microparticle reagents prepared by mixing of "High Reactivity Reagent PSA-124 nm-36G12/47F10" and "Low Reactivity Reagent PSA-124 nm-63C5/16B1" in the following ratios (v/v): 100/0; 90/10; 75/25; 50/50; 25/75; 0/100.

The ratio of the DLs of the calibration curves between the "High Reactivity Reagent PSA-124 nm-36G12/47F10" and "Low Reactivity Reagent PSA-124 nm-63C5/16B1" was 0.07 (see Table 2b).

FIG. 1A represents the variation of the DR as a function of the % (v/v) "High Reactivity Reagent PSA-124 nm-36G12/47F10".

The following Table 2b gives the DL, UML and DR for the above mixing ratios expressed in % (v/v) of "High Reactivity Reagent PSA-124 nm-36G12/47F10", and in the concentration of particles of 124 nm diameter coated with high reactivity monoclonal antibody 36G12 or 47F10 and the concentration of particles of 124 nm diameter coated with low reactivity monoclonal antibody 63C5 or 16B1. The best results in the DR were obtained for a microparticle reagent containing 50/50 (v/v) "High Reactivity Reagent PSA-124 nm-36G12/47F10", wherein the factor of increase of the DR compared to "Low Reactivity Reagent PSA-124 nm-63C5/16B1" and "High Reactivity Reagent PSA-124 nm-36G12/47F10" is about 1130/360 and about 1130/152, that is, about 3.1 and 7.1, respectively. For the reagent containing 50/50 (v/v) of "High Reactivity Reagent PSA-124 nm-36G12/47F10", the DL was about 16.6 ng/ml.

TABLE 2a

Calibration curve data for microparticle reagents of particles of 124 nm diameter coated separately with high reactivity mab 36G12 or 47F10 ("High Reactivity Reagent PSA-124 nm-36G12/47F10"), particles of diameter 124 nm coated with low reactivity mab 63C5 or 16B1 ("Low Reactivity Reagent PSA-124 nm-63C5/16B1") and the 50/50 v/v mixture thereof ("Mixed Reactivity Reagent PSA-124 nm-36G12/47F10-63C5/16B1")

| ng/ml | $10^{-14}$ mol/cuvette | "High Reactivity Reagent-PSA-124 nm 36G12/47F10" | "Low Reactivity Reagent PSA-124 nm 63C5/16B1" | "Mixed Reactivity Reagent PSA-124 nm-36G12/47F10-63C5/16B 1" |
|---|---|---|---|---|
| 0 | 0 | −0.002 | −0.002 | 0.001 |
| 10.75 | 0.5 | 0.004 | −0.004 | 0.002 |
| 21.5 | 1.0 | 0.013 | −0.003 | 0.009 |
| 43.0 | 2.0 | 0.019 | −0.001 | 0.015 |
| 86 | 4.0 | 0.04 | −0.002 | 0.032 |
| 172 | 8.0 | 0.091 | 0.005 | 0.062 |
| 344 | 16 | 0.16 | 0.01 | 0.115 |
| 1032 | 48 | 0.333 | 0.028 | 0.239 |
| 3096 | 144 | 0.427 | 0.094 | 0.368 |
| 9310 | 433 | 0.458 | 0.238 | 0.472 |
| 18640 | 867 | 0.463 | 0.351 | 0.523 |
| 27950 | 1300 | 0.465 | 0.365 | 0.525 |

TABLE 2b

Detection limit (DL), upper measuring limit (UML) and dynamic range (DR) for a mixture of microparticle reagents of particles of 124 nm diameter coated with low reactivity mab 63C5 or 16B1 ("Low Reactivity Reagent PSA-124 nm-63C5/16B1"), and of particles of 124 nm diameter coated with high reactivity mab 36G12 or 47F10 ("High Reactivity Reagent PSA-124 nm-36G12/47F10")

| | PSA Concentration | | Optical density (GD) | | |
|---|---|---|---|---|---|
| % (v/v) of the "High Reactivity Reagent PSA-124nm-36G12/47F10" | Concentration of particles of 124 nm diameter coated with high reactivity mab 36G12 or 47F10 (% w/v) | Concentration of particles of 124 nm diameter coated with low reactivity mab 63C5 or 16B1 (% (w/v) | DL (ng/ml) | UML (ng/ml) | DR |
| 0% | 0 | 0.2 | 122.6 | 18640 | 152 |
| 10% | 0.02 | 0.18 | 19.4 | 18640 | 963 |
| 25% | 0.05 | 0.15 | 19.4 | 18640 | 963 |
| 50% | 0.1 | 0.1 | 16.6 | 18640 | 1130 |
| 75% | 0.15 | 0.05 | 8.6 | 9309 | 1083 |
| 90% | 0.18 | 0.02 | 8.6 | 9309 | 1083 |
| 100% | 0.2 | 0 | 8.6 | 3096 | 360 |

4) Mixing of Particles of Different Sizes Coated with Antibodies of Different Reactivities a) Mixing of 221 nm Diameter Particles Coated with High Reactivity Antibodies and 124 nm Diameter Particles Coated with Low Reactivity Antibodies Microparticle reagents, hereafter referred to as "High Reactivity Reagent PSA-221 nm-36G12/47F10" and "Low Reactivity Reagent PSA-124 nm-63C5/16B1", were prepared by mixing equal volumes of microparticle reagent of particles of diameter 221 nm coated with high reactivity monoclonal antibody 36G12 and microparticle reagent of particles of diameter 221 nm coated with high reactivity monoclonal antibody 47F10, and by mixing equal volumes of microparticle reagent of particles of diameter 124 nm coated with low reactivity monoclonal antibody 63C5 and microparticle reagent of particles of diameter 124 nm coated with low reactivity monoclonal antibody 16B1, respectively.

The calibration curves were plotted and the DL, UML and DR were determined for microparticle reagents prepared by mixing of "High Reactivity Reagent PSA-221 nm-36G12/47F10" and "Low Reactivity Reagent PSA-124 nm-63C5/16B1" in the following ratios (v/v): 100/0; 90/10; 75/25; 50/50; 25/75; 0/100.

The following Table 3a gives the DL, UML and DR for the above mixing ratios expressed in % (v/v) of the "High Reactivity Reagent PSA-221 nm-36G12/47F10", and in the concentration of particles of 221 nm diameter coated with high reactivity monoclonal antibody 36G12 or 47F10 and the concentration of particles of 124 nm diameter coated with low reactivity monoclonal antibody 63C5 or 16B1.

FIG. 1B represents the variation of the DR as a function of the % (v/v) of "High Reactivity Reagent PSA-221 nm-36G12/47F10".

The data contained in Table 3a and FIG. 1B show that a surprisingly high increase of the DR is obtained by mixing according to the invention particles of different sizes coated with antibodies of different reactivities. For a mixture of about 75% (v/v) of the "High Reactivity Reagent PSA-221 nm-36G12/47F10", the factor of increase of the DR with respect to the "High Reactivity Reagent PSA-221 nm-36G12/47F10" and the "Low Reactivity Reagent PSA-124 nm-36G12/47F10", is about 8600/200 and about 8600/152, that is, about 43 and about 57, respectively. The DR is thus significantly extended compared to each of the tests "High Reactivity Reagent PSA-221 nm-36G12/47F10" and "Low Reactivity Reagent PSA-124 nm-63C5/16B1", the factor of increase of the DL being significantly higher than that obtained when mixing particles of 124 nm diameter coated with high affinity mab 36G12 or 47F10 and particles of 124 nm diameter coated with low affinity mab 63C5 or 16B1 (about 3.1 and about 7.1, as set forth above). At the same time, the mixture of about 75% (v/v) of the "High Reactivity Reagent PSA-221 nm-36G12/47F10", provides a DL of about 1.07 ng/l CRP, that is, about 15 times lower than that obtained when mixing particles of 124 nm diameter coated with high affinity mab 36G12 or 47F10 and particles of 124 nm diameter coated with low affinity mab 63C5 or 16B1 (about 16.6 ng/l, as set forth above).

16B1" in the following ratios (v/v): 100/0; 90/10; 75/25; 50/50; 25/75; 0/100.

The following Table 3b gives the DL, UML and DR for the above mixing ratios expressed in % (v/v) of the "High Reactivity Reagent PSA-221 nm-36G12/47F10", and in the concentration of particles of 221 nm diameter coated with high reactivity monoclonal antibody 36G12 or 47F10 and the concentration of particles of 89 nm diameter coated with low reactivity monoclonal antibody 63C5 or 16B1.

Figure 1C:
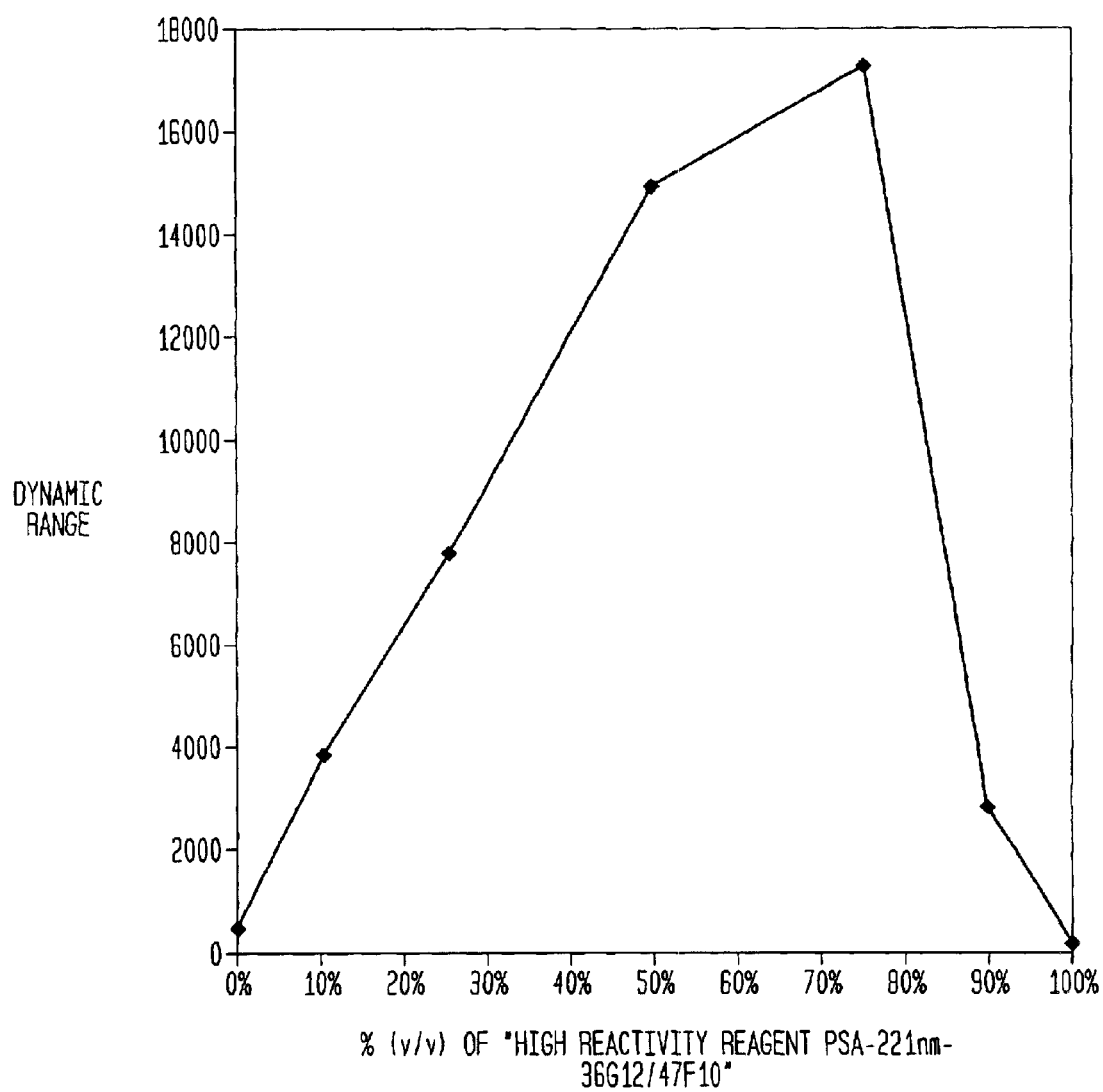
FIG. 1C represents the variation of the DR of a mixture of microparticle reagents: a 1/1 mixture of particles of 89 nm diameter coated with low reactivity monoclonal antibody 63C5 or 16B1 ("Low Reactivity Reagent PSA-89 nm-63C5/16B1"), and a 1/1 mixture of particles of 221 nm diameter coated with high reactivity antibody 36G12 or 47F10 ("High Reactivity Reagent PSA-221 nm-36G12/47F10"), as a function of the % (v/v) of the latter microparticle reagent.

FIG. 1C represents the variation of the DR as a function of the % (v/v) of "High Reactivity Reagent PSA-221 nm-36G12/47F10".

The data contained in Table 3b and FIG. 1C show that a surprisingly high increase of the DR is obtained by mixing according to the invention particles of different sizes coated with antibodies of different reactivities. For a mixture of about 75% (v/v) of the "High Reactivity Reagent PSA-221 nm-36G12/47F10", the factor of increase of the DR with TABLE 3a Detection limit (DL), upper measuring limit (UML) and dynamic range (DR) for a mixture of microparticle reagents of particles of 124 nm diameter coated with low reactivity mab 63C5 or 16B1 ("Low Reactivity Reagent PSA-124 nm-63C5/16B1"), and of particles of 221 nm diameter coated with high reactivity mab 36G12 or 47F10 ("High Reactivity PSA 221 nm-36G12/47F10")

| % (v/v) of the "High Reactivity Reagent PSA-221 nm-36G12/47F10" | Concentration of particles of 221 nm diameter (% w/v) | Concentration of particles of 124 nm diameter (% w/v) | DL (ng/ml) | UML (ng/ml) | DR |
|---|---|---|---|---|---|
| 0% | 0 | 0.2 | 122.6 | 18600 | 152 |
| 10% | 0.01 | 0.18 | 19.3 | 18600 | 963 |
| 25% | 0.025 | 0.15 | 6.4 | 18600 | 2890 |
| 50% | 0.05 | 0.1 | 2.1 | 9310 | 4330 |
| 75% | 0.075 | 0.05 | 1.07 | 9310 | 8600 |
| 90% | 0.09 | 0.02 | 0.86 | 3096 | 3600 |
| 100% | 0.1 | 0 | 0.86 | 172 | 200 | b) Mixing of 221 nm Diameter Particles Coated High Reactivity Antibodies and 89 nm Diameter Particles Coated with Low Reactivity Antibodies Microparticle reagents, hereafter referred to as "High Reactivity Reagent PSA-221 nm-36G12/47F10" and "Low Reactivity Reagent PSA-89 nm-63C5/16B1", were prepared by mixing equal volumes of microparticle reagent of particles of diameter 221 nm coated with high reactivity monoclonal antibody 36G12 and microparticle reagent of particles of diameter 221 nm coated with high reactivity monoclonal antibody 47F10, and by mixing equal volumes of microparticle reagent of particles of diameter 89 nm coated with low reactivity monoclonal antibody 63C5 and microparticle reagent of particles of diameter 89 nm coated with low reactivity monoclonal antibody 16B1, respectively.

The calibration curves were plotted and the DL, UML and DR were determined for microparticle reagents prepared by mixing of "High Reactivity Reagent PSA-221 nm-36G12/47F10" and "Low Reactivity Reagent PSA-89 nm-63C5/ respect to the "High Reactivity Reagent PSA-221 nm-36G12/4710" and the "Low Reactivity Reagent PSA-89 nm-63C5/16B1", is about 17300/200 and about 17300/650, that is, about 86.5 and about 27, respectively. The DR is thus significantly extended compared to each of the tests "High Reactivity Reagent PSA-221 nm-36G12/47F10" and "Low Reactivity Reagent PSA-124 nm-63C5/16B1", the factor of increase of the DL being significantly higher than that obtained when mixing particles of 124 nm diameter coated with high affinity mab 36G12 or 47F10 and particles of 124 nm diameter coated with low affinity mab 63C5 or 16B1 (about 3.1 and about 7.1, as set forth above). At the same time, a mixture of about 75% (v/v) of the "High Reactivity Reagent PSA-221 nm-36G12/47F10", provides a DL of about 1.07 ng/l CRP, that is, about 15 times lower than that obtained when mixing particles of 124 nm diameter coated with high affinity mab 36G12 or 47F10 and particles of 124 nm diameter coated with low affinity mab 63C5 or 16B1 (about 16.6 ng/l, as set forth above).

TABLE 3b

Detection limit (DL), upper measuring limit (UML) and dynamic range (DR) for a mixture of microparticle reagents of particles of 89 nm diameter coated with low reactivity mab 63C5 or 16B1 ("Low Reactivity Reagent PSA-89 nm-63C5/16B1"), and of particles of 221 nm diameter coated with high reactivity mab 36G12 or 47F10 ("High Reactivity Reagent PSA-221 nm-36G12/47F10")

| % (v/v) of the "High Reactivity Reagent PSA-221 nm-36G12/47F10" | Concentration of particles of 221 nm diameter (% (w/v) | Concentration of particles of 89 nm diameter (% (w/v) | DL (ng/ml) | UML (ng/ml) | DR |
|---|---|---|---|---|---|
| 0% | 0 | 0.5 | 86 | 56000 | 650 |
| 10% | 0.01 | 0.45 | 11 | 42000 | 3900 |
| 25% | 0.025 | 0.375 | 5.4 | 42000 | 7800 |
| 50% | 0.05 | 0.25 | 2.8 | 42000 | 15000 |
| 75% | 0.075 | 0.125 | 1.07 | 18600 | 17300 |
| 90% | 0.09 | 0.05 | 1.07 | 3100 | 2900 |
| 100% | 0.1 | 0 | 0.86 | 172 | 200 |

Figure 2:
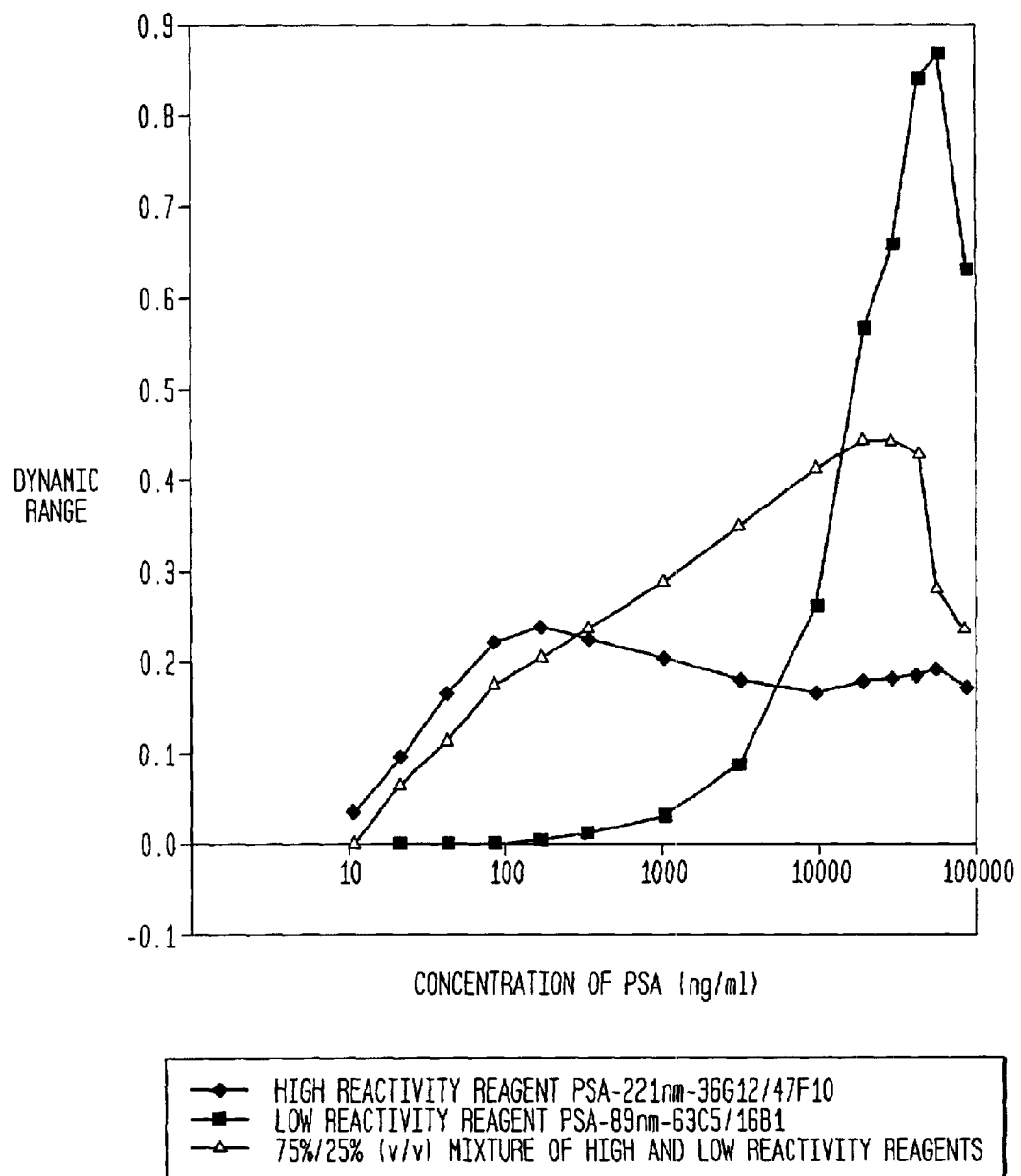
FIG. 2 represents the calibration curves of the "High Reactivity Reagent PSA-221 nm-36G12/47F10", the "Low Reactivity Reagent PSA-89 nm-63C5/16B1 " and their 75/25 (v/v) mixture.

FIG. 2 represents the calibration curves of "High Reactivity Reagent PSA-221 nm-36G12/47F10", "Low Reactivity Reagent PSA-89 nm-63C5/16B1" and their 75/25 (v/v) mixture. That figure shows how the mixture surprisingly combines the advantageous properties of each of those microparticle reagents: steep curve for low concentrations of PSA corresponding to a high DL for the reagent of particles of 221 nm diameter coated with a high reactivity monoclonal antibody, and steep curve for high concentrations of PSA corresponding to a high UML for the microparticle reagent of particles of 89 nm diameter coated with a low reactivity monoclonal antibody.

5) Mixing of Large Particles Co-Coated with a Pair of High Reactivity Antibodies and Small Particles Co-Coated with a Pair of Low Reactivity Antibodies A microparticle reagent of 221 nm diameter particles co-coated with high reactivity mabs 36G12 and 47F11, hereafter referred to as "High Reactivity Reagent 124 nm-PSA-36G12-co-47F10", and a microparticle reagent of 89 nm particles co-coated with low reactivity mabs 63C5 and 16B1, hereafter referred to as "Low Reactivity Reagent PSA-89 nm-63C5-co-16B1", were prepared as described above under 1) b), with the difference that during the coating an equimolar mixture of the pair of high reactivity mabs or low reactivity mabs was used instead of a single mab.

The calibration curves were plotted and the DL, UML and DR were determined for microparticle reagents prepared by mixing of "High Reactivity Reagent PSA-221 nm-36G12-co-47F10" and "Low Reactivity Reagent PSA-89 nm-63C5-co-16B1" in the following ratios (v/v): 100/0; 90/10; 75/25; 50/50; 25/75; and 0/100.

The following Table 3c gives the DL, UML and DR for the above mixing ratios expressed in % (v/v) of the "High Reactivity Reagent PSA-221 nm-36G12-co-47F10", and in the concentration of particles of 221 nm diameter co-coated with high reactivity monoclonal antibodies 36G12 and 47F10 and the concentration of particles of 89 nm diameter co-coated with low reactivity monoclonal antibodies 63C5 and 16B 1.

The data contained in Table 3c show that an surprisingly high increase of the DR is obtained by mixing according to the invention particles of different sizes coated with antibodies of different reactivities. For a mixture of about 75% (v/v) of the "High Reactivity Reagent PSA-221 nm-36G12-co-47F10", the factor of increase of the DR with respect to the "High Reactivity Reagent PSA-221 nm-36G12-co-47F10" and the "Low Reactivity Reagent PSA-89 nm-36G12-co-47F10", is about 10200/154 and about 10200/250, that is, about 66 and about 41, respectively. The DR is thus significantly extended compared to each of the tests "High Reactivity Reagent PSA-221 nm-36G12-co-47F10" and "Low Reactivity Reagent PSA-124 nm-63C12-co-16B1", the factor of increase of the DL being significantly higher than that obtained when mixing particles of 124 nm diameter coated with high affinity mab 36G12 or 47F10 and particles of 124 nm diameter coated with low affinity mab 63C5 or 16B1 (about 3.1 and about 7.1, as set forth above).

TABLE 3c

Detection limit (DL), upper measuring limit (UML) and dynamic range (DR) for a mixture of the "Low Reactivity Reagent PSA-89 nm-63C5-co-16B1" and the "High Reactive Reagent PSA-221 nm-36G12-co-47F10"

| % (v/v) of the "High Reactivity Reagent PSA-221 nm-36G12-47F10" | Concentration of particles of 221 nm diameter co-coated with 36G12 and 47F10 (%) | Concentration of particles of 89 nm diameter co-coated with 63C5 and 16B1 (%) | DL (ng/ml) | UML (ng/ml) | DR |
|---|---|---|---|---|---|
| 0% | 0 | 0.5 | 111 | 27970 | 250 |
| 10% | 0.01 | 0.45 | 31.8 | 27970 | 880 |
| 25% | 0.025 | 0.375 | 6.0 | 27970 | 4643 |
| 50% | 0.05 | 0.25 | 3.3 | 27970 | 8387 |
| 75% | 0.075 | 0.125 | 1.8 | 9309 | 10200 |

TABLE 3c-continued

Detection limit (DL), upper measuring limit (UML) and dynamic range (DR) for a mixture of the "Low Reactivity Reagent PSA-89 nm-63C5-co-16B1" and the "High Reactive Reagent PSA-221 nm-36G12-co-47F10"

| % (v/v) of the "High Reactivity Reagent PSA-221 nm-36G12-47F10" | Concentration of particles of 221 nm diameter co-coated with 36G12 and 47F10 (%) | Concentration of particles of 89 nm diameter co-coated with 63C5 and 16B1 (%) | DL (ng/ml) | UML (ng/ml) | DR |
|---|---|---|---|---|---|
| 90% | 0.09 | 0.05 | 1.3 | 9309 | 6984 |
| 100% | 0.1 | 0 | 1.1 | 172 | 154 |

EXAMPLE 2

Increase of the dynamic range of a microparticle enhanced light scattering immunoagglutination assay for C-reactive protein (CRP).

1) Methods and Reagents a) Preparation of Monoclonal Antibodies to CRP Having Different Affinities.

C-reactive protein (CRP) is an acute-phase serum component that is clinically used for screening local or general inflammation and for tracking therapeutic accuracy. CRP is a nonglycosylated 115 kDa protein composed of five identical 23 kDa subunits arranged in a closed circular array.

Monoclonal antibodies to CRP were prepared by methods well known in the art, described for example by Harlow et al, 1988, Section 6 of "Antibodies: a Laboratory Manual", Cold Spring Harbor Press, New York, USA. Mice were immunized in regular intervals with 4 injections of 50 µg of purified human CRP obtained by a method comprising calcium-dependent affinity chromatography, reverse affinity chromatography and gel filtration, as described by D. M. Vigushi et al, 1993, J. Clin. Invest. 91, 1351–1357. Three months after the first injection lymphocytes isolated from the spleen of the immunized mice were fused with the myeloma cell line SP2/0-Ag14 (ATCC CRL 1581) using the polyethyleneglycol method as described by G. Galfré et al., 1981, Methods in Enzymology 73, 3–46.

Hybridomas secreting an antibody against CRP, were identified by the following screening ELISA: microtiter-plates were coated with rabbit anti-human-CRP immuno-globulin. CRP bound to this solid phase was incubated with the supernatants of the hybridoma cultures. Monoclonal antibody bound to CRP was detected using anti-mouse-immunoglobulin-peroxidase-conjugate.

5 hybridomas could thus be isolated which secrete antibodies against at least 3 different epitopes of human CRP. One of these epitopes is only accessible in the presence of calcium. The monoclonal antibodies were purified and were characterized in more detail.

Epitope binding analysis was performed and the relative reactivity of the antibodies was determined in terms of their apparent dissociation constants, using the BIAcore™ biosensor technology (Pharmacia, Sweden). The latter is based on the surface plasmon resonance technique (see J. L. Daiss et al., 1994, in "Methods: A Companion to Methods in Enzymology" 6, 143–156, Academic Press Inc., New York, USA) and allows one to monitor the kinetics and stochiometry of biomolecular reactions. Starting from cell culture supernatants, the monoclonal antibodies were bound to the biosensor surface via polyclonal rabbit anti-mouse-Fc-antibody. Association and dissociation of the antigen CRP to the monoclonal antibodies were monitored. The data were analyzed using the inherent BIA evaluation software, based on the simple A+B=AB equilibrium model, without consideration of the five repetitive epitopes of the antigen CRP (L. G. Fägerstam et al., 1992, Journal of Chromatography, 597, 397–410).

High affinity monoclonal antibody 36F12 having an apparent dissociation constant of 0.13 nM and low affinity monoclonal antibody 8A12 having an apparent dissociation constant of 1.2 nM were selected for coating the microparticles. Those monoclonal antibodies recognize non overlapping epitopes of CRP. The hybridomas producing monoclonal antibodies 36F12 and 8A12 were deposited in accordance with the Budapest Treaty on Jun. 2, 1997 at the DSMZ under the numbers ACC23 11 and ACC2312, respectively.

b) Preparation of Microparticle Reagents

The same coating procedure as in Example 1 1) b) was used with the above monoclonal antibodies and carboxy-modified polystyrene spherical particles having respectively a diameter of 89, 124 or 221 nm (available from Seradyn Inc., Indianapolis, USA, under reference numbers C9553/20, 2280 and 532G).

After the last centrifugation step the microparticle pellet was resuspended in the above buffer by tip sonication and diluted to a working concentration depending on the size of microparticle, namely for a diameter of 89 nm, 0.5% w/v, for a diameter of 124 nm, 0.2% w/v and for a diameter of 221 nm, 0.1% w/v. That working concentration was chosen so as to have an optical density (OD) blank value at cycle 5 between 0.35 and 0.45, as in Example 1 1) b).

c) Determination of the Calibration Curve and Calculation of the DL, UML and DR

All measurements of immunoagglutination reactions were performed on a COBAS® MIRA S clinical chemistry analyzer (Hoffmann-La-Roche A. G., Basel, Switzerland), using the same reaction buffer and the same parameter setting as in Example 1 1)c).

The DL, UML and DR were statistically determined as in Example 1 1) c).

2) Influence of Microparticle Size on the Calibration Curve

The calibration curves were plotted and the DL, UML and DR were determined for microparticle reagents of particles of diameter 89, 124 or 221 nm coated with the same amount of the same antibody to CRP, namely either high reactivity monoclonal antibody 36F12 or low reactivity monoclonal antibody 8A12.

The following Tables 4a and 4b respectively set forth the optical density (OD) measured as a function of the CRP concentration (that is, the calibration curve data), and the DL, UML and DR for two such microparticle reagents, one of particles of diameter 89 nm coated with monoclonal antibody 36F12, the other of particles of diameter 221 nm coated with monoclonal antibody 36F12, and the 25/75 (v/v) mixture thereof.

As illustrated in Table 4b, for particles of diameter 89 nm and particles of diameter 221 nm, the DL and the UML both decreased with particle size, as could be expected from the Rayleigh scattering theory. The particles of diameter 221 nm show a preferable low detection limit of 0.016 mg/l CRP, but insufficient UML and DR due to the limited concentration of microparticles in the assay. (Increasing the concentration would lead to an unacceptably high blank value).

3) Influence of Antibody Reactivity on the Calibration Curve

Microparticle reagents, hereafter referred to as "High Reactivity Reagent 124 nm-CRP-36F12" and "Low Reactivity Reagent CRP-124 nm-8A12", were prepared by coating respectively particles of diameter 124 nm with high reactivity monoclonal antibody 36F12 and particles of diameter 124 nm with low reactivity monoclonal antibody 8A12. "High Reactivity Reagent 124 nm-CRP-36F12" and "Low Reactivity Reagent CRP-124 nm-8A12" were mixed in the following ratios (v/v): 100/0; 90/10; 75/25; 50/50; 25/75; 0/100.

TABLE 4a

Calibration curve data for microparticle reagents of particles of 89 or 221 nm diameter coated with high reactivity mab 36F12 and their 25/75 (v/v) mixture.

| CRP concentration | | Optical density (OD) | | |
|---|---|---|---|---|
| ng/ml | $10^{-14}$ mol/cuvette | Particles of 89 nm diameter | Particles of 221 nm diameter | Particles of 89 and 221 nm diameter (25/75 v/v mixture) |
| 0 | 0 | −0.002 | −0.02 | 0 |
| 0.021 | 0.28 | −0.003 | 0.008 | −0.002 |
| 0.041 | 0.56 | 0 | 0.016 | −0.005 |
| 0.083 | 1.1 | 0.002 | 0.052 | 0.002 |
| 0.17 | 2.25 | 0.001 | 0.135 | 0.007 |
| 0.33 | 4.5 | 0.007 | 0.301 | 0.019 |
| 0.66 | 9 | 0.017 | 0.379 | 0.039 |
| 2 | 27 | 0.065 | 0.364 | 0.146 |
| 6 | 81 | 0.253 | 0.338 | 0.402 |
| 18 | 243 | 0.833 | 0.336 | 0.498 |
| 36 | 486 | 1.073 | 0.355 | 0.483 |
| 54 | 729 | 1.098 | 0.362 | 0.501 |
| 81 | 1094 | 1.1 | 0.373 | 0.466 |
| 108 | 1458 | 1.095 | 0.378 | 0.428 |
| 161 | 2187 | 1.077 | 0.380 | 0.384 |

TABLE 4b

Detection limit (DL), upper measuring limit (UML) and dynamic range (DR) for microparticle reagents of particles of 89 or 221 nm diameter coated with high reactivity mab 36F12 and the 25/75 (v/v) mixture thereof

| | DL (mg/l) | UML (mg/l) | DR |
|---|---|---|---|
| Particles of diameter 89 nm | 0.18 | 36 | 200 |
| Particles of diameter 221 nm | 0.016 | 0.66 | 41 |
| Particles of 89 and 221 nm diameter (25/75 v/v mixture) | 0.088 | 18 | 205 |

Mixing the particles of diameter 89 nm and diameter 221 nm results in only a very slight increase of the DR compared to that of the particles of diameter 89 nm, with a maximum value of about 205, obtained with a 25/75 (v/v) mixture of 89 nm and 221 nm particles, hereafter referred to as "High Reactivity Reagent CRP-89 nm/221 nm-36F12", showing a relatively high detection limit of about 0.09 mg/l.

The calibration curves (see raw data in Table 5a) were plotted and their DL, UML and DR were determined.

The ratio of the DLs of the calibration curves between the "High Reactivity Reagent 124 nm-CRP-36F12" and "Low Reactivity Reagent CRP-124 nm-8A12" was 0.29 (see Table 5b).

Figure 3A:
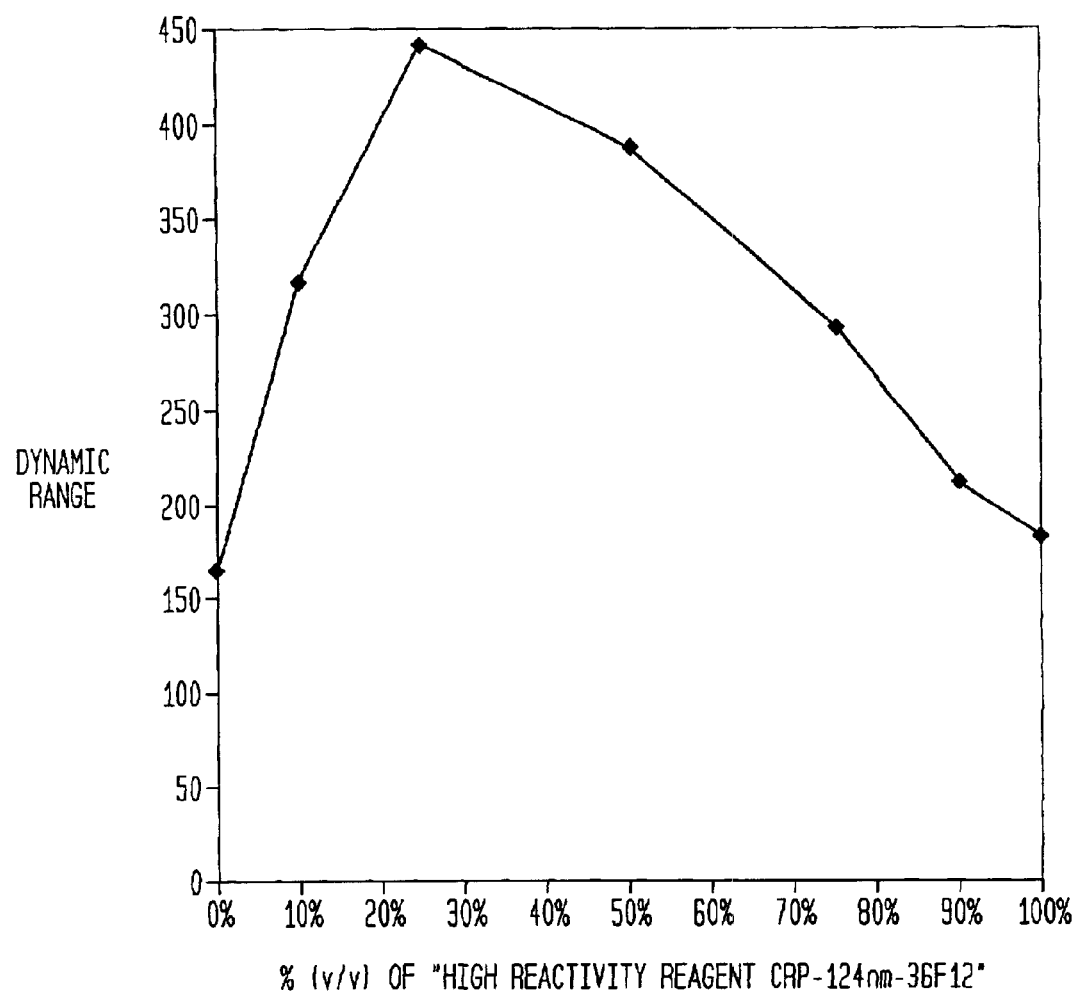
FIG. 3A represents the variation of the DR of a mixture of particles of 124 nm diameter coated with antibodies to CRP of different reactivities, as a function of the % (v/v) of the microparticle reagent particles coated with high reactivity monoclonal antibody 36F12 ("High Reactivity Reagent CRP-124 nm-36F12").

FIG. 3A represents the variation of the DR as a function of the % (v/v) of "High Reactivity Reagent 124 nm-CRP-36F12".

The following table 5b sets forth the DL, UML and DR for the above mixing ratios expressed in % (v/v) of "High Reactivity Reagent CRP-124 nm-36F12", and in the concentration of particles of 124 nm diameter coated with high reactivity monoclonal antibody 36F12 and in the concentration of particles of 124 nm coated with low reactivity monoclonal antibody 8A12. The best results in the DR were obtained for a microparticle reagent containing 25/75 (v/v) "High Reactivity Reagent CRP-124 nm-36F12", hereafter referred to as "Mixed Reactivity Reagent CRP-124 nm-36F12/8A12", wherein the factor of increase of the DR compared to "High Reactivity Reagent CRP-124 nm-36F12" and the "Low Reactivity Reagent CRP-124 nm-8A12" was about 444/186 and 444/164, that is, about 2.4 and 2.7, respectively. The "Mixed Reactivity Reagent CRP-124 nm-36F12/8A12" showed a DL of about 0.08 mg/l CRP.

TABLE 5a

Calibration curve data for microparticle reagents of particles of 124 nm diameter coated with high reactivity mab 36F12 ("High Reactivity Reagent CRP-124 nm-36F12"), particles of diameter 124 nm coated with low reactivity mab 8A12 ("Low Reactivity Reagent CRP-124 nm-8A12") and the 25/75 v/v mixture thereof ("Mixed Reactivity Reagent CRP 124 nm-36F12/8A12").

| CRP concentration | | Optical density (OD) | | |
|---|---|---|---|---|
| mg/l | $10^{-14}$ mol/cuvette | "High Reactivity Reagent CRP-124 nm-36F12" | "Low Reactivity Reagent CRLP-124 nm-8A12" | "Mixed Reactivity Reagent CRP-124 nm-36F12/8A12 |
| 0 | 0 | 0 | −0.004 | 0 |
| 0.021 | 0.28 | 0.001 | −0.003 | 0 |
| 0.041 | 0.56 | 0.001 | −0.002 | −0.003 |
| 0.083 | 1.1 | 0.003 | −0.003 | 0.002 |
| 0.17 | 2.25 | 0.012 | −0.001 | 0.007 |
| 0.33 | 4.5 | 0.023 | 0.001 | 0.016 |
| 0.66 | 9 | 0.062 | 0.006 | 0.0038 |
| 2 | 27 | 0.166 | 0.025 | 0.129 |
| 6 | 81 | 0.367 | 0.097 | 0.315 |
| 18 | 243 | 0.461 | 0.265 | 0.489 |
| 36 | 486 | 0.468 | 0.393 | 0.551 |
| 54 | 729 | 0.467 | 0.435 | 0.565 |

TABLE 5b

Detection limit (DL), upper measuring limit (UML) and dynamic range (DR) for a mixture of microparticle reagents of particles of 124 nm diameter coated with low reactivity mab 8A12 ("Low Reactivity Reagent CRP-124 nm-8A12") and of particles of 124 nm diameter coated with high reactivity mab 36F12 ("High Reactivity Reagent CRP-124 nm-36F12")

| % (v/v) of "High Reactivity Reagent CRP-124 nm-36F12" | Concentration of particles of 124 nm diameter coated with high reactivity mab 36F12 (% w/v) | Concentration of particles of 124 nm diameter coated with low reactivity mab 8A12 (% w/v) | DL (mg/l) | UML (mg/l) | DR |
|---|---|---|---|---|---|
| 0% | 0 | 0.2 | 0.33 | 54 | 164 |
| 10% | 0.01 | 0.18 | 0.167 | 54 | 323 |
| 25% | 0.025 | 0.15 | 0.081 | 36 | 444 |
| 50% | 0.05 | 0.1 | 0.092 | 36 | 391 |
| 75% | 0.075 | 0.05 | 0.061 | 36 | 295 |
| 90% | 0.09 | 0.02 | 0.084 | 18 | 214 |
| 100% | 0.1 | 0 | 0.097 | 18 | 186 |

4) Mixing of Particles of Different Sizes Coated with Antibodies of Different Reactivities Microparticle reagents, hereafter referred to as "High Reactivity Reagent 221 nm-CRP-36F12" and "Low Reactivity Reagent CRP-89 nm-8A12", were prepared by coating respectively particles of diameter 221 nm with high reactivity monoclonal antibody 36F12 and particles of diameter 89 nm with low reactivity monoclonal antibody 8A12. "High Reactivity Reagent 221 nm-CRP-36F12" and "Low Reactivity Reagent CRP-89 nm-8A12" were mixed in the following ratios (v/v): 100/0; 90/10; 75/25; 50/50; 25/75; 0/100.

The calibration curves were plotted and the DL, UML and DR were calculated for microparticle reagents obtained by mixing a microparticle reagent of 89 nm particles coated with low reactivity monoclonal antibody 8A12 ("Low Reactivity Reagent CRP-89 nm-8A12"), and a microparticle reagent of 221 nm particles coated with high reactivity monoclonal antibody 36F12 ("High Reactivity Reagent CRP-221 nm-36F12"), according to the following ratios (v/v): 100/0; 50/50; 25/75; 10/90 and 0/100.

The following Table 6 gives the DL, UML and DR for the above mixing ratios expressed in the % (v/v) of the "High Reactivity Reagent CRP-221 nm-36F12", and in the concentration of particles of 221 nm diameter coated with high reactivity monoclonal antibody 36F12 and the concentration of particles of 89 nm diameter coated with low reactivity monoclonal antibody 8A12.

Figure 3B:
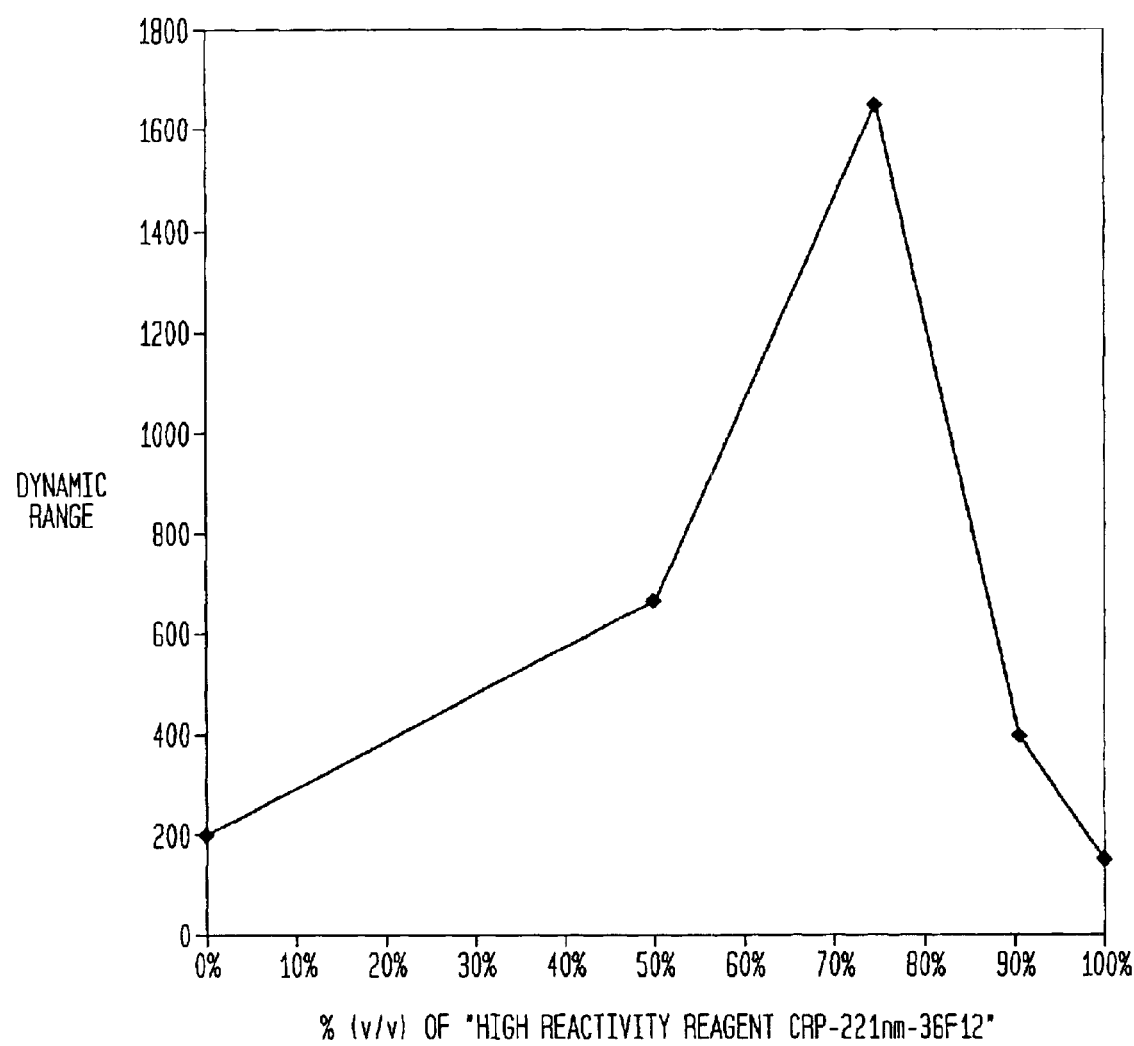
FIG. 3B represents the variation of the DR of a mixture of microparticle reagents of particles of 89 nm diameter coated with a low reactivity antibody to CRP ("Low Reactivity Reagent CRP-89 nm-8A12") and of particles of 221 nm diameter coated with a high reactivity antibody to CRP ("High Reactivity Reagent CRP-221 nm-36F 12"), as a function of the % (v/v) of the latter microparticle reagent.

FIG. 3B represents the variation of the DR as a function of the % (v/v) of the "High Reactivity Reagent CRP-221 nm-36F12".

The data contained in Table 6 and FIG. 3B show that a surprisingly high increase of the DR is obtained by mixing according to the invention particles of different sizes coated with antibodies of different reactivities. For a mixture of about 75% (v/v) of the "High Reactivity Reagent CRP-221 nm-36F12", the factor of increase of the DR with respect to the "High Reactivity Reagent CRP-89 nm/221 nm-36F12" and "Mixed Reactivity Reagent CRP-124 nm-36F12/8A12" is about 1640/200 and 1640/444, that is, about 8.2 and 3.7, respectively. The DR is thus significantly extended compared to each of the tests "High Reactivity Reagent CRP-89 nm/221 nm-36F12" and "High Reactivity Reagent CRP-124 nm-36F12", the factor of increase of the DL being significantly higher than that obtained when mixing particles of 124 nm diameter coated with low affinity mab 8A12 and particles of 124 nm diameter coated with high affinity mab 36F12 (about 2.4 to about 2.7, as set forth above). At the same time, the mixture of about 75% (v/v) of the "High Reactivity Reagent CRP-221 nm-36F12" provides a DL of about 0.022 mg/l CRP, that is, almost 4 times lower than that obtained when mixing particles of 124 nm diameter coated with low affinity mab 8A12 and particles of 124 nm diameter coated with high affinity mab 36F12 (about 0.08 mg/l, as set forth above).

TABLE 6

Detection limit (DL), upper measuring limit (UML) and dynamic range (DR) for a mixture of microparticle reagents of particles of 89 nm diameter coated with low reactivity mab 8A12 ("Low Reactivity Reagent CRP-89 nm-8A12") and particles of 221 nm diameter coated with high reactivity mab 36F12 ("High Reactivity Reagent CRP-221 nm-36F12")

| % (v/v) of "High Reactivity Reagent CRP-221 nm-36F12" | Concentration of particles of 221 nm diameter (% w/v) | Concentration of particles of 89 nm diameter (% w/v) | DL (mg/l) | UML (mg/l) | DR |
|---|---|---|---|---|---|
| 0% | 0 | 0.5 | 0.41 | 81 | 198 |
| 50% | 0.05 | 0.25 | 0.081 | 54 | 670 |
| 75% | 0.075 | 0.125 | 0.022 | 36 | 1640 |
| 90% | 0.09 | 0.05 | 0.015 | 6 | 400 |
| 100% | 0.1 | 0 | 0.015 | 2 | 133 |

Figure 4:
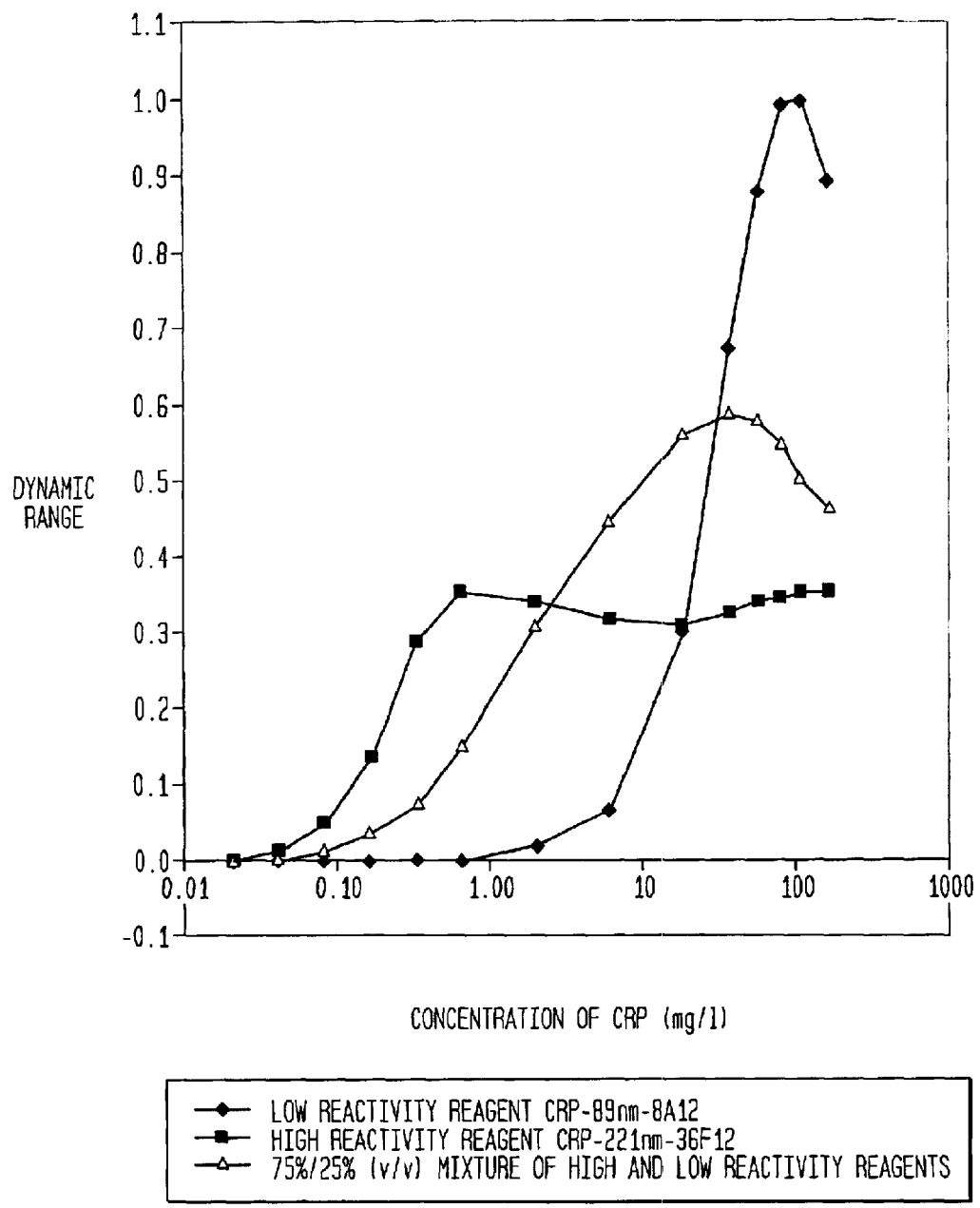
FIG. 4 represents the calibration curves of the "Low Reactivity Reagent CRP-89 nm-8A12", the "High Reactivity Reagent CRP-221 nm-36F12", and their 75/25 (v/v) mixture.

FIG. 4 represents the calibration curves of the "High Reactivity Reagent CRP-221 nm-36F12", the "Low Reactivity Reagent CRP-89 nm-8A12", and their 75/25 (v/v) mixture according to the invention. That figure shows how the mixture unexpectedly combines the advantageous properties of each of those microparticle reagents: steep curve for low concentrations of CRP corresponding to a high DL for the "High Reactivity Reagent CRP-221 nm-36F12", and steep curve for high concentrations of CRP corresponding to a high UML for the "Low Reactivity Reagent CRP-89 nm-8A12".

What is claimed is:

1. A reagent for an agglutination assay for determining an analyte in a sample, said reagent comprising a mixture of microparticles, said mixture comprising first microparticles having a mean diameter from 30 to 600 nm and a refractive index, wherein said first microparticles are coated with a first binding partner for said analyte, and second microparticles having a mean diameter from 30 to 600 nm and a refractive index, wherein said second microparticles are coated with a second binding partner for said analyte, said first microparticles having stronger light scattering properties than said second microparticles, and said first binding partner having a higher reactivity for said analyte than said second binding partner, said microparticles being capable of causing light scattering at wavelengths between 300 and 1200 nm.

2. The reagent of claim 1, wherein said mean diameter of said first microparticles is greater than said mean diameter of said second microparticles.

3. The reagent of claim 2, wherein said refractive index of said first microparticles is greater than said refractive index of said second microparticles.

4. The reagent of claim 3, wherein a ratio of the mean diameter of said first microparticles to the mean diameter of said second microparticles ranges from about 1.5 to about 4.0.

5. The reagent of claim 1, wherein said first microparticles and said second microparticles have a concentration ratio in said mixture of from about 0.01 to about 5.0.

6. The reagent of claim 1, wherein said analyte is a nucleic acid and said first and second binding partners are oligonucleotide capture probes.

7. The reagent of claim 1, wherein said analyte is antigenic and said first and second binding partners are monoclonal antibodies or fragments thereof.

8. The reagent of claim 1, wherein said first and second microparticles have a composition selected from the group consisting of selenium, carbon, gold, a nitride of carbon, a nitride of silicium, a nitride of germanium, an oxide of iron, an oxide of titanium, an oxide of silicium, an epoxy resin, polyvinyl chloride, polyvinylidene chloride, polyalphanaphthylmethacrylate, polvinylnaphthalene polystyrene and a copolymer thereof.

9. The reagent of claim 1, wherein the analyte is C-reactive protein and the first and second binding partners recognize different epitopes of C-reactive protein.

10. The reagent of claim 1, wherein the analyte is prostate specific antigen and the first and second binding partners recognize different epitopes of prostate specific antigen.

* * * * *